(12) United States Patent
Yu et al.

(10) Patent No.: US 10,426,850 B2
(45) Date of Patent: Oct. 1, 2019

(54) COLLAGEN MIMETIC PEPTIDES FOR TARGETING COLLAGEN STRANDS FOR IN VITRO AND IN VIVO IMAGING AND THERAPEUTIC USE

(71) Applicant: The Johns Hopkins University, Baltimore, MD (US)

(72) Inventors: Michael S. Yu, Timonium, MD (US); Yang Li, Baltimore, MD (US); Daniel Summerfield, Baltimore, MD (US); Allen Yi-Lan Wang, Belle Mead, NJ (US); Catherine A. Foss, Baltimore, MD (US); Martin G. Pomper, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/679,431

(22) Filed: Nov. 16, 2012

(65) Prior Publication Data
US 2013/0164220 A1 Jun. 27, 2013

Related U.S. Application Data

(60) Provisional application No. 61/562,639, filed on Nov. 22, 2011, provisional application No. 61/693,447, filed on Aug. 27, 2012.

(51) Int. Cl.
*A61K 49/00* (2006.01)
*A61K 38/39* (2006.01)
(Continued)

(52) U.S. Cl.
CPC .......... *A61K 49/0056* (2013.01); *A61K 38/39* (2013.01); *C07K 14/78* (2013.01);
(Continued)

(58) Field of Classification Search
CPC ........ A61K 38/00; A61K 38/16; A61K 38/39; A61K 39/39541; A61K 49/0056;
(Continued)

(56) References Cited

U.S. PATENT DOCUMENTS 5,849,323 A 12/1998 Braswell et al.
8,283,414 B2 * 10/2012 Yu .......................... A61K 38/10
514/17.2
(Continued)

FOREIGN PATENT DOCUMENTS

WO WO2007/044026 A2 * 4/2007
WO WO2009018126 A2 * 2/2009

OTHER PUBLICATIONS

Takaki Koide. Designed triple-helical peptides as tools for collagen biochemistry and matrix engineering. Phil. Trans. R. Soc. B (2007) 362, 1281-1291.*
(Continued)

*Primary Examiner* — Marcela M Cordero Garcia
*Assistant Examiner* — Jia-Hai Lee
(74) *Attorney, Agent, or Firm* — John Hopkins Technology Ventures

(57) ABSTRACT

The present invention provides both a caged collagen mimetic peptide (CCMP) having the formula: L-S-$Z_m$-[Gly-X-Y]$_n$-$^L$Gly-X-Y-[Gly-X-Y]$_n$ (SEQ ID NO: 19); wherein L is one or more detectable moieties; S is one or more spacer molecules; $Z_m$ is any amino acid where m is an integer of 1 to 10; X is proline or modified proline; Y is proline or modified proline; Gly is glycine; n is an integer from 1 to 20; and $^L$Gly is a glycine covalently linked to a cage moiety comprising a labile protecting group, as well as a collagen mimetic peptides lacking the labile protecting group (CMP). The inventions are useful for binding collagen and denatured collagen and/or gelatin both in vitro and in vivo, and are useful for targeting any organ or tissue where collagen is present, and can be used for research and diagnostic imaging (both in vivo and in vitro) and also for in vivo therapeutic applications.

13 Claims, 31 Drawing Sheets

(51) Int. Cl.
*C07K 14/78* (2006.01)
*G01N 33/68* (2006.01)
*A61K 38/00* (2006.01)

(52) U.S. Cl.
CPC .......... *G01N 33/6887* (2013.01); *A61K 38/00* (2013.01); *Y02P 20/55* (2015.11)

(58) Field of Classification Search
CPC ........ A61K 49/0043; A61K 8/64; A61K 8/65; A61K 49/0017; A61K 49/0002; C07K 1/13; C07K 14/47; C07K 2317/21; C07K 14/78; C12Q 2563/107; G01N 33/582; C07H 19/20
See application file for complete search history.

(56) References Cited

U.S. PATENT DOCUMENTS 8,883,964 B2 * 11/2014 Yu .......................... A61K 38/10
525/54.1
2008/0287342 A1 11/2008 Yu et al.

OTHER PUBLICATIONS

Persikov et al. Amino Acid Propensities for the Collagen Triple-Helix. Biochemistry 2000, 39, 14960-14967.*
Politou et al. The elastic I-band region of titin is assembled in a "modular" fashion by weakly interacting Ig-like domains. J Mol Biol. Feb. 2, 1996;255(4):604-16.*
IRDye-800CW Technical Note. LI-COR Biociences 2008.*
Tian et al. Synthesis of chlorinated fluoresceins for labeling proteins. Bioorg. Med. Chem. Lett. 18 (2008) 1977-1979.*
Beppu et al. Single Benzene Green Fluorophore: Solid-State Emissive, Water-Soluble, and Solvent- and pH-Independent Fluorescence with Large Stokes Shifts. Angew. Chem. Int. Ed. 2015, 54, 7332-7335.*
Sun et al. Selective disruption of early/recycling endosomes: release of disulfide-linked cargo mediated by a N-alkyl-3beta-cholesterylamine-capped peptide. J Am Chem Soc. Aug. 6, 2008;130(31):10064-5. (Year: 2008).*
Yu, et al., "Collagen mimetic peptides: progress towards functional applications", Soft Matter, Jun. 7, 2011, vol. 7 pp. 7927-7938.
Lee, et al., "Collagen mimetic peptide-conjugated photopolymerizable PEG hydrogel", Biomaterials, Oct. 2006, vol. 27, No. 30, pp. 5268-5276.
Cretu, et al., "Impact of the non-cellular tumor microenvironment on metastasis: potential therapeutic and imaging opportunities", Journal of Cellular Physiology, Nov. 2007, vol. 213, No. 2, pp. 391-402.
International Search Report and The Written Opinion of the International Search Authority dated Mar. 29, 2013 for application PCT/US2012/065551.
Tatsu, et al., FEBS Letters, vol. 525 pp. 20-24 (2002).
Stahl, et al., Analytical Biochemistry, vol. 424 pp. 137-139 (2012).
Li, et al., Biopolymers vol. 95, pp. 94-104 (2011).
Horng, et al. Organic Letters, vol. 8, No. 21, pp. 4735-4738 (2006).
Berisio, et al., Biopolymers, vol. 73,682-688 (2004).
Judge, et al. The Journal of Clinical Investigation, vol. 114, pp. 172-181 (2004).
Mohs, et al., The Journal of Biological Chemistry, vol. 282, No. 41, pp. 29757-29765, (2007).
Nandy, et al., Organic Letters, vol. 9, No. 12, pp. 2249-2252 (2007).

* cited by examiner

FIGURE 19
Peptide 1: IR800-Ahx<sup>NB</sup>(GPO)₉
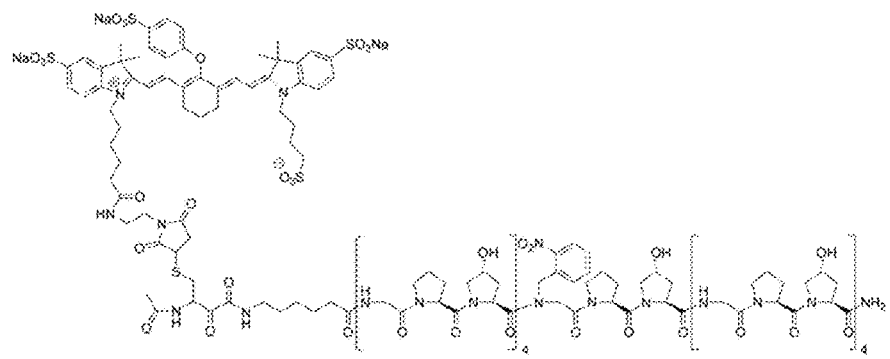
Peptide 2: IR680-Ahx<sup>NB</sup>(GPO)₉
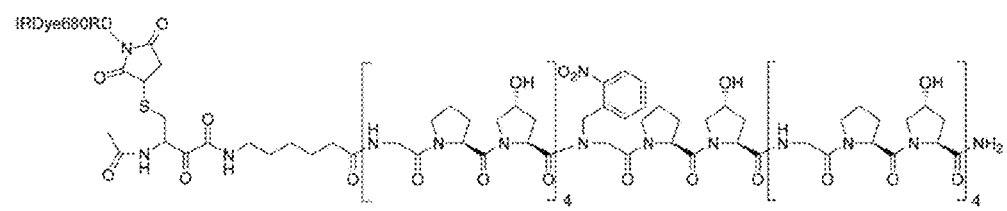
Peptide 3: I-Y-Ahx-<sup>NB</sup>(GPO)₉
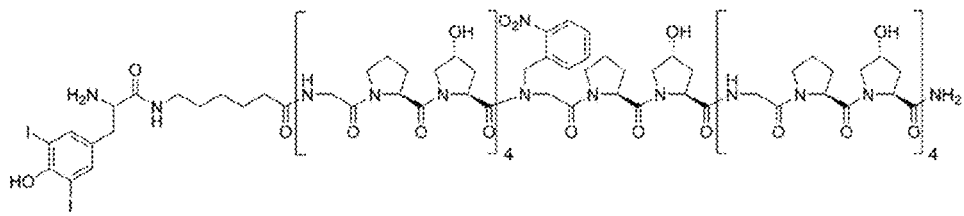
Peptide 4: dual IR680-DTPA-Ahx-<sup>NB</sup>(GPO)₉
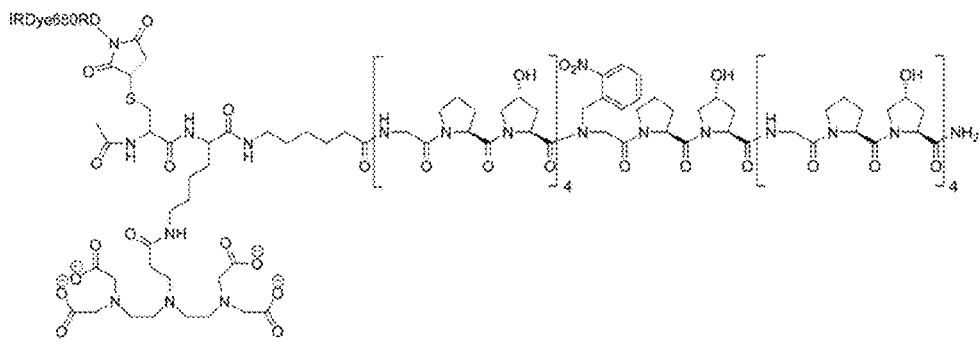

MALDI-ToF MS of peptides 1-4.

| CMP | | m/z calculated | m/z found | # |
|---|---|---|---|---|
| IR800-Ahx-$^{NB}$(GPO)$_9$ | [M + H$^+$] | 3939 | 3911 | 1 |
| IR680-Ahx-$^{NB}$(GPO)$_9$ | [M + Na$^+$] | 3786 | 3785 | 2 |
| I-Y-Ahx-$^{NB}$(GPO)$_9$ | [M + Na$^+$] | 3108 | 3107 | 3 |
| dual IR680-DTPA-Ahx-$^{NB}$(GPO)$_9$ | [M + Na$^+$] | 4308 | 4304 | 4 |
| dual IR680-DTPA[In$^{3+}$]-Ahx-$^{NB}$(GPO)$_9$ | [M + Na$^+$] | 4417 | 4416 | |

MALDI-ToF spectra of peptides 1-3.

FIGURE 21

MALDI-ToF spectra of peptide 4

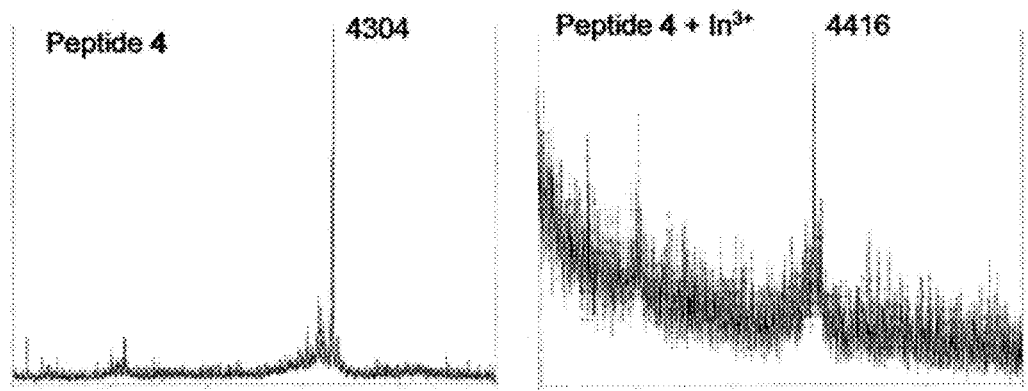

HPLC purification of peptides 1-4.

| CMP | target peak elusion time (min) | mobile phase gradient slope | # |
|---|---|---|---|
| IR800-Ahx-$^{NB}$(GPO)$_9$ | 21.2 | 13-27% MeCN in 28 min | 1 |
| IR680-Ahx-$^{NB}$(GPO)$_9$ | 22.1 | 13-30% MeCN in 34 min | 2 |
| I-Y-Ahx-$^{NB}$(GPO)$_9$ | 12.9 | 15-40% MeCN in 25 min | 3 |
| dual IR680-DTPA-Ahx-$^{NB}$(GPO)$_9$ | 22.3 | 13-26% MeCN in 26 min | 4 |

HPLC method:
Peptide products were purified by reverse phase HPLC on a Vydac C18 column using a linear gradient mixture of water (0.1% TFA) and acetonitrile (MeCN, 0.1% TFA) at a flow rate of 1 mL/min under room temperature, monitored by 275 nm UV absorbance.

HPLC traces of peptides 1-4 in the final purification steps.

Circular dichroism (CD) spetra and melting curve of peptide 3 before and after UV exposure.

FIGURE 27A
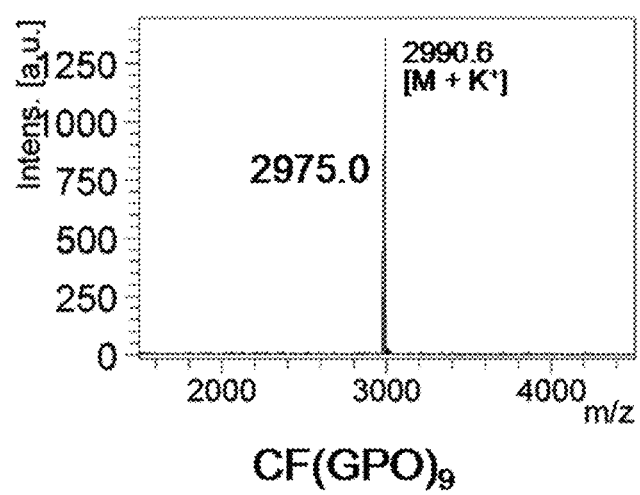
CF(GPO)₉
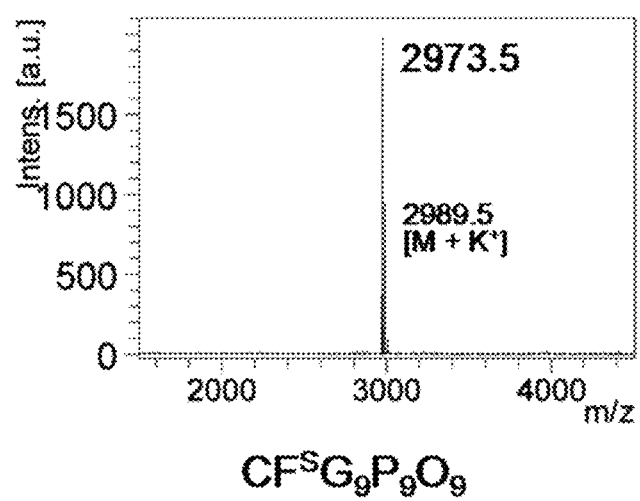
CF^S G₉P₉O₉

FIGURE 27B
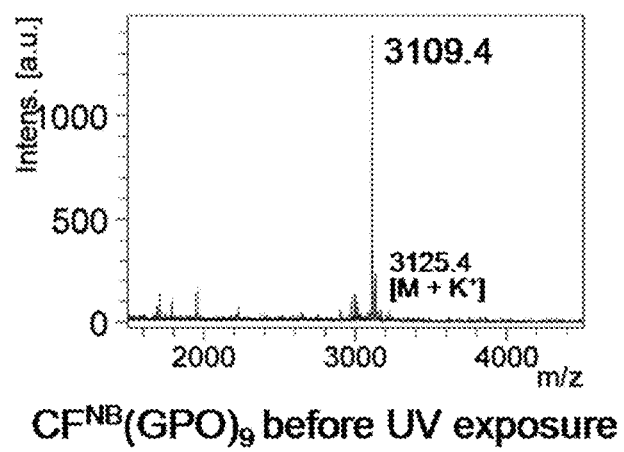
CF$^{NB}$(GPO)$_9$ before UV exposure
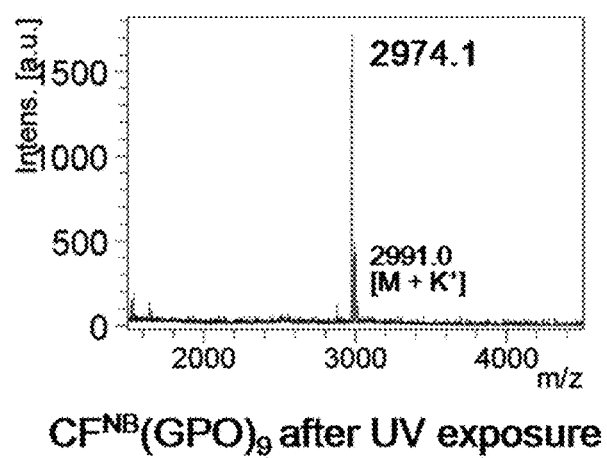
CF$^{NB}$(GPO)$_9$ after UV exposure

US 10,426,850 B2

COLLAGEN MIMETIC PEPTIDES FOR TARGETING COLLAGEN STRANDS FOR IN VITRO AND IN VIVO IMAGING AND THERAPEUTIC USE

REFERENCE TO RELATED APPLICATIONS

This application claims the benefit of U.S. Provisional Patent Application Nos. 61/562,639, filed on Nov. 22, 2011, and 61/693,447, filed Aug. 27, 2012, both of which are hereby incorporated by reference for all purposes as if fully set forth herein.

STATEMENT OF GOVERNMENTAL INTEREST

This invention was made with government support under grant no. GM074812, CA092871, AR060484 and DMR0645411 awarded by the National Institutes of Health and the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jul. 19, 2019, is named P11749-04_SL.txt and is 34,632 bytes in size.

BACKGROUND OF THE INVENTION

As the most abundant protein in mammals, collagens play a crucial role in tissue development and regeneration, and their structural or metabolic abnormalities are associated with debilitating genetic diseases and various pathologic conditions. Although collagen remodeling occurs during development and normal tissue maintenance, particularly for renewing tissues (e.g. bones), excess remodeling activity is commonly seen in tumors, arthritis, and many other chronic wounds. During collagen remodeling, large portions of collagens are degraded and denatured by proteolytic enzymes which can be explored for diagnostic and therapeutic purpose. Since unstructured proteins are not ideal targets for rational drug design, library approaches have been employed to develop monoclonal antibody and peptide probes that specifically bind to cryptic sites in collagen strands that become exposed when denatured. However, these probes suffer from poor pharmacokinetics, and/or low specificity and binding affinity.

Fibrous collagens are major structural components of extracellular matrix in mammals; collagen overproduction is associated with many human diseases including cancers and fibrosis. Collagen is typically identified in biomedical research by western blot and immunohistochemistry; however anti-collagen antibodies employed in these analyses are difficult to prepare and their affinities to collagen can diminish if collagen becomes denatured during analyses.

Thus, there exists a need for new probes and techniques for detection of collagens both in vitro, using direct detection methods for gels and histology, as well as in vivo detection for collagens undergoing remodeling and therapeutics based on the same.

SUMMARY OF THE INVENTION

In accordance with an embodiment, the present invention provides a caged collagen mimetic peptide (CCMP) having the formula:

L-S-[Gly-X-Y]$_n$-$^L$Gly-X-Y-[Gly-X-Y]$_n$;     (SEQ ID NO: 1)

wherein L is one or more detectable moieties and/or a biologically active compound; S is one or more spacer molecules; X is proline or modified proline; Y is proline or modified proline; Gly is glycine; n is an integer from 1 to 20; and $^L$Gly is a glycine covalently linked to a cage moiety comprising a labile protecting group.

In accordance with an embodiment, the present invention provides a caged collagen mimetic peptide (CCMP) having the formula:

L-S-[Gly-X-Y]$_n$-$^{PL}$Gly-X-Y-[Gly-X-Y]$_n$;     (SEQ ID NO: 2)

wherein L is one or more detectable moieties and/or a biologically active compound; S is one or more spacer molecules; X is proline or modified proline; Y is proline or modified proline; Gly is glycine; n is an integer from 1 to 20; and $^{PL}$Gly is a glycine covalently linked to a cage moiety comprising a photolabile protecting group.

In accordance with another embodiment, the present invention provides a collagen mimetic peptide (CMP) having the formula:

L-S-[Gly-X-Y]$_n$-Gly-X-Y-[Gly-X-Y]$_n$;     (SEQ ID NO: 3)

wherein L is one or more detectable moieties and/or a biologically active compound; S is one or more spacer molecules; X is proline or modified proline; Y is proline or modified proline; Gly is glycine; and n is an integer from 1 to 20.

In accordance with a further embodiment, the present invention provides a collagen mimetic peptide conjugate comprising: a) the CCMP or CMP described above; and b) an active agent selected from the group consisting of: an antibiotic, a cell adhesion molecule, a contrast agent, a detectable label, a growth factor, a component of the extracellular matrix, an anti-inflammatory, a polymer, PEG, a biologically active compounds, and a small molecule. It will be understood by those of ordinary skill that such biologically active compounds and small molecules would include, for example, growth factor inhibitors, and proteinase inhibitors.

In accordance with yet another embodiment, the present invention provides a nanoparticle comprising the CCMP or CMP described above, fixed to the nanoparticle.

In accordance with an embodiment, the present invention provides a method for detection of collagen in a subject comprising: a) administering to the subject an effective amount of the CCMP or CMP described above, or a collagen mimetic peptide conjugate, or a nanoparticle; b) allowing the collagen mimetic peptide, or conjugate or nanoparticle sufficient time to bind collagen and/or gelatin in the subject; and c) detecting the collagen mimetic peptide, or conjugate or nanoparticle in the subject.

In accordance with another embodiment, the present invention provides a method for detection of collagen remodeling by MMP and/or other enzymes in a subject comprising: a) administering to the subject an effective amount of the CCMP or CMP described above, or a collagen mimetic peptide conjugate, or a nanoparticle; b) allowing the collagen mimetic peptide, or conjugate or nanoparticle sufficient time to bind collagen and/or gelatin in the subject; and c) detecting the collagen mimetic peptide, or conjugate or nanoparticle in the subject.

In accordance with a further embodiment, the present invention provides a method for detection of pathologic tissues having high proteinase (e.g., MMP) activity in a subject comprising: a) administering to the subject an effective amount of the CCMP or CMP described above, or a collagen mimetic peptide conjugate, or a nanoparticle; b)

allowing the collagen mimetic peptide, or conjugate or nanoparticle sufficient time to bind collagen and/or gelatin in the subject; and c) detecting the collagen mimetic peptide, or conjugate or nanoparticle in the subject.

In accordance with still another embodiment, the present invention provides a method for detection of collagen remodeling in bones and cartilage in a subject comprising: a) administering to the subject an effective amount of the CCMP or CMP described above, or a collagen mimetic peptide conjugate, or a nanoparticle; b) allowing the collagen mimetic peptide, or conjugate or nanoparticle sufficient time to bind collagen and/or gelatin in the subject; and c) detecting the collagen mimetic peptide, or conjugate or nanoparticle in the subject.

In accordance with yet another embodiment, the present invention provides a method for detection of musculoskeletal disease in a subject comprising: a) administering to the subject an effective amount of the CCMP or CMP described above, or a collagen mimetic peptide conjugate, or a nanoparticle; b) allowing the collagen mimetic peptide, or conjugate or nanoparticle sufficient time to bind collagen and/or gelatin in the subject; and c) detecting the collagen mimetic peptide, or conjugate or nanoparticle in the subject.

In accordance with an embodiment, the present invention provides a method for treatment of a disease associated with collagen denaturation or remodeling in a subject comprising administering to the subject an effective amount of a collagen mimetic peptide conjugate, or a nanoparticle to treat the disease in the subject.

In accordance with another embodiment, the present invention provides a method for detection of collagen or a protein having a collagen like domain in a substrate comprising: a) contacting the substrate with an effective amount of a solution comprising the collagen mimetic peptide or a collagen mimetic peptide conjugate described above, wherein the solution is pre-heated to a temperature above the melting point of the collagen mimetic peptide; b) allowing the collagen mimetic peptide, or conjugate sufficient time to bind collagen and/or gelatin in the substrate at a temperature below the melting point of the collagen mimetic peptide; and c) detecting the collagen mimetic peptide, or conjugate in the substrate.

In accordance with a further embodiment, the present invention provides a method for detection of collagen or a protein having a collagen like domain in a substrate comprising: a) contacting the substrate with an effective amount of a solution comprising the caged collagen mimetic peptide or a caged collagen mimetic peptide conjugate as described above; b) activating the caged collagen mimetic peptide or conjugate; c) allowing the activated collagen mimetic peptide, or conjugate sufficient time to bind collagen and/or gelatin in the substrate; and c) detecting the collagen mimetic peptide, or conjugate in the substrate.

In accordance with a further embodiment, the present invention provides a method for detection of collagen or a protein having a collagen like domain in a substrate comprising: a) contacting the substrate with an effective amount of a solution comprising the caged collagen mimetic peptide or a caged collagen mimetic peptide conjugate as described above; b) exposing the substrate in the solution of a) to UV light for sufficient time to caged collagen mimetic peptide or conjugate to be activated; c) allowing the activated collagen mimetic peptide, or conjugate sufficient time to bind collagen and/or gelatin in the substrate; and c) detecting the collagen mimetic peptide, or conjugate in the substrate.

BRIEF DESCRIPTION OF THE DRAWINGS

FIG. 1 discloses SEQ ID NOS 4 and 10, respectively, in order of appearance.

FIG. 3B discloses SEQ ID NOS 9 and 8, respectively, in order of appearance. (C) Epifluorescence micrographs of the unfixed PC-3 tumor sections from (B), additionally stained in vitro with anti-Col 2¾C$_{short}$ antibody (green) and anti-CD31-PE antibody conjugate (red). IR-Ahx-(GPO)$_9$ (SEQ ID NO: 9) (blue) co-localized partially with anti-Col 2¾C$_{short}$ antibody (green) particularly within the peri-vasculatures. No such co-localization was detected for the control peptide (scale bars: 100 μm). FIG. 3C discloses SEQ ID NOS 9 and 8, respectively, in order of appearance.

FIG. 4D discloses SEQ ID NO: 9. (E) Whole body NIRF images of mouse model with Marfan syndrome 96 hr after IR'-Ahx-(GPO)$_9$ (SEQ ID NO: 9) administration showing high CMP uptake in the skeleton of the diseased mouse. Whole body images were taken after skin removal.

FIG. 6 discloses SEQ ID NOS 20-23, 4, and 4, respectively, in order of appearance.

FIG. 14 discloses SEQ ID NOS 9 and 8, respectively, in order of appearance.

FIG. 15A discloses SEQ ID NOS 9 and 8, respectively, in order of appearance. (B) Images of the harvested tumors and legs (containing tibias with femur heads) from both mice, showing uptake of only IR-Ahx-(GPO)$_9$ (SEQ ID NO: 9). Fluorescence intensity is shown in rainbow scale with images scaled to the same exposure time. FIG. 15B discloses SEQ ID NOS 9 and 8, respectively, in order of appearance.

FIG. 16 discloses SEQ ID NOS 9 and 8, respectively, in order of appearance.

FIG. 19 shows molecular structures of four CCMP embodiments (peptides 1-4) of the present invention. FIG. 19 discloses SEQ ID NOS 7, 7, 16 and 7, respectively, in order of appearance.

FIG. 20 discloses SEQ ID NOS 7, 7, 16, 7, and 7, respectively, in order of appearance.

FIG. 21 shows MADLI-TOF spectra for CCMP peptide 4 of the present invention, and HPLC purification data for CCMP peptides 1-4. FIG. 21 discloses SEQ ID NOS 7, 7, 16 and 7, respectively, in order of appearance.

FIGS. 27A-27C depict MALDI-TOF Mass spectra of fluorescently labeled CMPs. FIGS. 27A-C disclose SEQ ID NOS 10, 5, 4, 4, 12, and 12, respectively, in order of appearance.

DETAILED DESCRIPTION OF THE INVENTION

Figure 1:
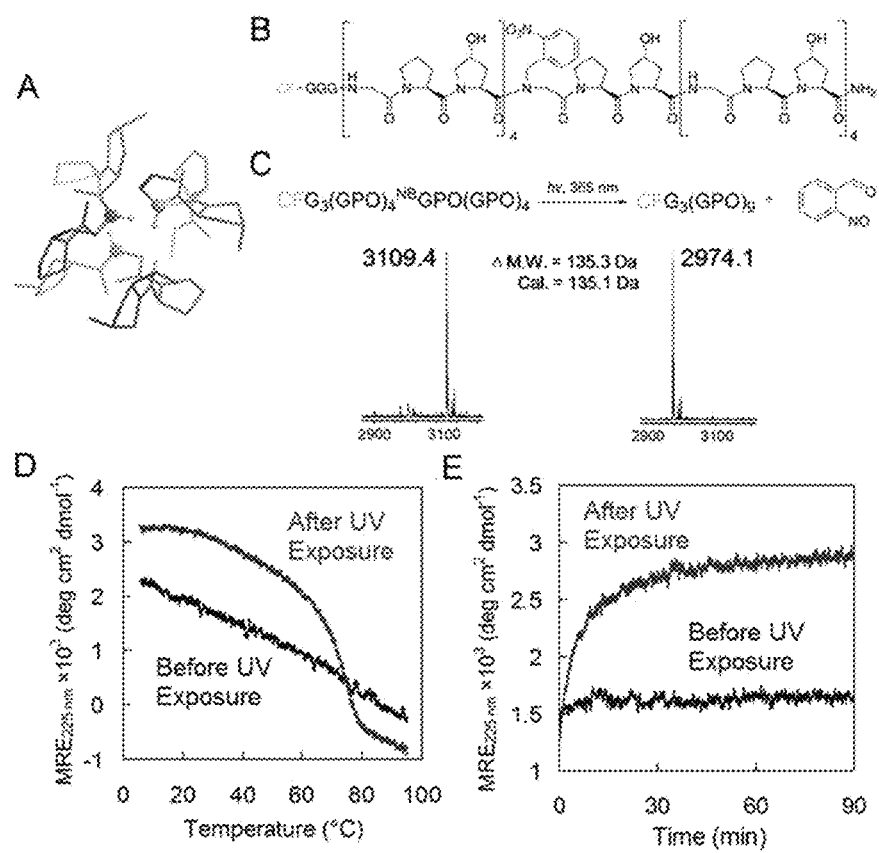
FIG. 1 depicts photo-triggered triple helical folding of caged CMPs. (A) The backbone NH groups of Gly (represented by the ball and stick model) play a key role in stabilizing the collagen triple helix. (B) Structure of $CF^{NB}(GPO)_9$ (SEQ ID NO: 4) featuring a photo-reactive nitrobenzyl (NB) group (in blue) conjugated to the central Gly. (C) Photo-cleavage of the NB cage group is monitored by MALDI-MS. (D, E) The NB cage group completely abolishes the triple helical folding capacity of $CF^{NB}(GPO)_9$ (SEQ ID NO: 4) and the photo-cleaving of the NB cage leads to CMP folding into stable triple helices, evidenced by CD melting studies (D) and refolding kinetics (E) of the peptides before and after UV exposure. For the refolding kinetic study (E), $CF^{NB}(GPO)_9$ (SEQ ID NO: 4) (before and after UV exposure) were thermally quenched from 80° C. to 25° C. and the change in CD ellipticity at 225 nm was monitored at 25° C.

In vivo use of caged CMP. In accordance with one or more embodiments, the present invention provides the design and synthesis of a new caged CMP that can be triggered to fold into triple helix by use of chemical, enzymatic, or photo based reactions. Using the new caged CMP, one can now compare the CMP's binding affinity to intact type I collagen as well as the same collagen denatured by heat or by matrix metalloproteinase (MMP) digestion, and also study its stereo-selective hybridization mechanism. The embodiments of the present invention further provide labeled CMPs that can be used in vivo to target and image denatured collagens in tissues undergoing remodeling either due to normal renewal process (e.g. bones and cartilages) or pathologic conditions such as tumor progression (e.g. prostate and pancreatic cancers) and musculoskeletal disease (e.g. Marfan syndrome).

The compositions and methods of the present invention provide for the first time the ability to directly interrogate structural remodeling of ECM by peptide hybridization. The CMPs of the present invention can be readily conjugated to imaging and therapeutic moieties. Therefore, the CMP mediated collagen strand targeting methods and compositions of the present invention opens new avenues, beyond tumor, bone and joint imaging, for applications in detection and treatment, both in vivo and in vitro, of a wide range of pathologic conditions associated with high MMP activity such as wound healing, ECM degeneration, and fibrous tissue formation.

In accordance with an embodiment, the present invention provides a caged collagen mimetic peptide (CCMP) having the formula: L-S-[Gly-X-Y]$_n$-$^L$Gly-X-Y-[Gly-X-Y]$_n$ (SEQ ID NO: 1); wherein L is one or more detectable moieties; S is one or more spacer molecules; X is proline or modified proline; Y is proline or modified proline; Gly is glycine; n is an integer from 1 to 20; and $^L$Gly is a glycine covalently linked to a cage moiety comprising a labile protecting group.

In accordance with an embodiment, the present invention provides a caged collagen mimetic peptide (CCMP) having the formula: L-S-[Gly-X-Y]$_n$-$^{PL}$Gly-X-Y-[Gly-X-Y]$_n$ (SEQ ID NO: 2); wherein L is one or more detectable moieties; S is one or more spacer molecules; X is proline or modified proline; Y is proline or modified proline; Gly is glycine; n is an integer from 1 to 20; and $^{PL}$Gly is a glycine covalently linked to a cage moiety comprising a photolabile protecting group.

As used herein, the term "proline or modified proline" means the amino acid proline and various isomers, analogs and variants thereof, including both natural and non-natural isomers. Examples of modified proline include, without limitation, hydroxyproline and 4-fluoro proline.

The term "caged" as used herein means that the CMP of the present invention has a labile protecting group linked to a glycine residue. Examples of labile protecting groups include, without limitation, photolabile groups (designated as a superscript "PL" herein), molecules containing carbonyl groups (carboxylic acids, ketones and aldehydes), amines, and hydroxy and thiol groups (any chemically or enzymatically labile group is included and is designated as a superscript "L" herein). Specific examples include o-nitrobenzyl groups, phenacyl groups, benzoin esters and Desyl compounds, o-nitrophenylethylene glycol compounds, benzyl alcohols, sulfonamides, and the like.

As used herein, the terms "CMP" meaning collagen mimetic peptide, can also be used collectively to include CCMPs as well.

As used herein, the term "spacer molecule or molecules" is one or more molecules or amino acids which are linked to the detectable moiety and the rest of the CCMP or CMP described above. In one embodiment, the spacer is any one or more amino acids designated as Z$_n$, where m is an integer of 1 to 10. In another embodiment, the spacer is aminohexanoic acid.

As used herein, the term "activating" a CCMP or conjugate means removing the caged group from the CMP molecule using a variety of means. In one or more embodiments, the caged group can be removed by UV light, heat, pH change, and enzymatic activity, for example.

In accordance with a further embodiment, the present invention provides a collagen mimetic peptide conjugate comprising: a) the CCMP or CMP described above; and b) an active agent selected from the group consisting of: an antibiotic, a cell adhesion molecule, a contrast agent, a detectable label, a growth factor, a component of the extracellular matrix, an anti-inflammatory, a polymer, PEG, a therapeutic compound, and a small molecule.

In accordance with another embodiment, the present invention provides a method for treatment of a disease associated with collagen denaturation or remodeling in a subject comprising administering to the subject an effective amount of a collagen mimetic peptide conjugate, or a nanoparticle to treat the disease in the subject.

In one or more embodiments, the CCMPs of the present invention are activated prior to administration in vivo to a subject. In other embodiments, the CCMPs of the present invention are activated after to administration in vivo to a subject.

The invention provides a simple means for delivering biologically active compounds (including nucleic acids, peptides, small molecule inhibitors, and mimetics) conjugated to a CMP or CCMP. The CMP or CCMP conjugate is capable of acting as a therapeutic for the treatment of a disease or disorder. A biologic agent conjugated to a collagen mimetic peptide and found to have medicinal value using the methods described herein is useful as a drug or as information for structural modification of existing compounds, e.g., by rational drug design. Desirably, the conjugates include antibiotics (e.g., penicillin, tetracycline, plectasin, LAH4), cell adhesion molecules (e.g., cadherin, fibronectin, integrin, laminin, selectin), growth factors that promote angiogenesis, cell growth, differentiation, proliferation, neurogenesis, osteogenesis, stem cell renewal, or cell survival (e.g., angiogenin, erythropoietin, vascular endothelial growth factor (VEGF), granulocyte/macrophage colony stimulating factor, macrophage-colony stimulating factor, platelet-derived endothelial cell growth factor, and platelet-derived growth factor), growth factor inhibitors (e.g., VEGF inhibitors), therapeutic compounds (e.g., anti-cancer drugs, anti-angiogenic drugs, etc.) or small molecules, such as antithrombotics (e.g., heparin-CMP, Hirudin-CMP, Saratin-CMP), anti-atherosclerosis agents, cartilage repair agents (e.g., chondroitin sulfate, glucosamine sulfate, hyaluronic acid), proteinase inhibitors (e.g., MMP inhibitors, cathepsin inhibitors). In other embodiments, the biologically active agents can agents which have bone health enhancing properties, such as, for example, anabolic agents, such as PTH (1-34), statins such as lovastatin and simvastatin, and bone morphogenetic protein-2 (BMP-2).

The polymers used including the collagen mimetic peptide conjugates are administered either as liquids or solids. Where the polymers are administered as a liquid, they are typically converted to a solid in vivo by cross-linking. Such crosslinking may be accomplished using any method known in the art, such as photopolymerization.

If desired, CMP or CCMP conjugates are incorporated into hydrogel-forming polymeric materials that are useful as drug delivery devices. Hydrogel-forming polymers are polymers that are capable of absorbing a substantial amount of water to form elastic or inelastic gels. Medical devices incorporating hydrogel-forming polymers are capable of being implanted in liquid or gelled form. Once implanted, the hydrogel forming polymer absorbs water and swells. The release of a pharmacologically active agent incorporated into the device using a collagen mimetic peptide takes place through this gelled matrix via a diffusion mechanism. Many hydrogels, although biocompatible, are not biodegradable or are not capable of being remodeled and incorporated into a host tissue. For therapeutic uses, the compositions or agents identified using the methods disclosed herein may be administered systemically.

In one embodiment, a CMP or CCMP conjugate is formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the subject. Treatment of subjects (e.g., human patients or other animals) will be carried out using a therapeutically effective amount of a CMP or CCMP therapeutic conjugate in a physiologically-acceptable carrier, such as a collagen matrix that includes the CMP or CCMP therapeutic conjugate. Suitable carriers and their formulation are described, for example, in Remington's Pharmaceutical Sciences by E. W. Martin. The amount of the therapeutic agent to be administered varies depending upon the manner of administration, the age and body weight of the subject, and with the clinical symptoms of the subject. Generally, amounts will be in the range of those used for other agents used in the treatment of similar diseases (e.g., thrombosis, atherosclerosis). A compound is administered at a dosage that controls the clinical or physiological symptoms of the disease as determined by a diagnostic method known to one skilled in the art.

In still other embodiments of any of the above aspects, the CMP or CCMP is conjugated to an antibiotic (e.g., penicillin, tetracycline, plectasin, LAH4), a cell adhesion molecule (e.g., cadherin, fibronectin, integrin, laminin, selectin), a contrast agent (e.g., a gadolinium complex, gadodiamide derivative, ferric ammonium citrate, and mangafodipar trisodium), a detectable label (e.g., a colloidal particle, an enzyme, an electron-dense reagent, a fluorescent dye, a hapten, an immunogen, a magnetic bead, a radiolabel, carboxy-fluorescein), a growth factor that promotes angiogenesis, cell growth, differentiation, proliferation, neurogenesis, osteogenesis, stem cell renewal, or cell survival, such as angiogenin, erythropoietin, vascular endothelial growth factor (VEGF), granulocyte/macrophage colony stimulating factor, macrophage-colony stimulating factor, platelet-derived endothelial cell growth factor, or platelet-derived growth factor, a component of the extracellular matrix (e.g., collagen, elastin, fibrillin, fibronectin, laminin; proteoglycans, hyaluronan, chondroitin sulfate, dermatan sulfate, heparan sulfate, heparin, keratan sulfate, and aggrecan), an anti-inflammatory (e.g., corticosteroids, NSAE)S), a polymer (e.g., collagen, poly(ethylene oxide) diacrylate (PEODA), poly(ethylene glycol) (PEG) (e.g., a star shaped PEG, a multi-armed PEG, a graft linear PEG, PEG2000, and PEG5000), and a small molecule, such as an anti-thrombotics (e.g., heparin-CMP, Hirudin-CMP, Saratin-CMP), atherosclerosis therapeutic (e.g., cholestyramine, colestipol, nicotinic acid, gemfibrozil, probucol, atorvastatin, lovastatin), a cartilage repair agent (e.g., chondroitan sulfate)), growth factor inhibitors (e.g. VEGF inhibitors) and proteinase inhibitors (MMP or cathepsin inhibitors). In various embodiments, the collagen mimetic peptide binds to any one or more collagen selected from the group consisting of type 1-29 collagen, such as type I, II, III, IV, IX, X, or XI.

In accordance with another embodiment, the present invention provides a CMP or CCMP conjugated to inhibitors of growth factors and proteinases.

By "collagen" is meant a protein component of an extracellular matrix having a tertiary structure that includes polypeptide chains intertwining to form a collagen triple helix or having a characteristic amino acid composition comprising Gly-X-Y repeat units, or a fragment thereof. Collagens useful in the methods of the invention include any collagen known in the art (e.g., one of collagen type 1-29). The term "collagen" also includes collagen that has been digested or denatured by enzymatic action, such as interaction with MMPs, and also includes gelatin, which is a denatured form of collagen.

A "collagen mimetic peptide conjugate" is a CMP or CCMP covalently bound to another molecule. Molecules capable of acting as CMP or CCMP conjugates include, but are not limited to, polypeptides, or fragments thereof, nucleic acid molecules, small molecule compounds, detectable labels, nanoparticles, and polymers.

By "ameliorate" is meant decrease, suppress, attenuate, diminish, arrest, or stabilize the development or progression of a disease.

By "alteration" is meant a change (increase or decrease) in the expression levels of a gene or polypeptide as detected by standard art known methods such as those described above. As used herein, an alteration includes a 10% change in expression levels, preferably a 25% change, more preferably a 40% change, and most preferably a 50% or greater change in expression levels."

"Biological sample" as used herein refers to a sample obtained from a biological subject, including sample of biological tissue or fluid origin, obtained, reached, or collected in vivo or in situ, that contains or is suspected of containing nucleic acids or polypeptides. Such samples can be, but are not limited to, organs, tissues, fractions and cells isolated from mammals including, humans such as a patient, mice, and rats. Biological samples also may include sections of the biological sample including tissues, for example, frozen sections taken for histologic purposes.

By "detectable label(s) or moieties" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. Specific radioactive labels include most common commercially available isotopes including, for example, $^{3}H$, $^{11}C$, $^{13}C$, $^{15}N$, $^{18}F$, $^{123}I$, $^{124}I$, $^{125}I$, $^{131}I$, $^{86}Y$, $^{89}Zr$, $^{111}In$, $^{94m}Tc$, $^{99m}Tc$, $^{64}Cu$ and $^{68}Ga$. Suitable dyes include any commercially available dyes such as, for example, 5(6)-carboxyfluorescein, IRDye 680RD maleimide or IRDye 800CW, ruthenium polypyridyl dyes, and the like.

One of ordinary skill in the art would understand that other diagnostic or therapeutic radionuclides could also be used that are known for ablation of malignant, atherosclerotic, or otherwise pathologic tissue. Examples of such radionuclides include $^{212}Bi$, $^{213}Bi$, $^{123}I$, $^{125}I$, $^{131}I$, $^{111}In$, $^{90}Y$, $^{211}At$, $^{177}Lu$, $^{203}Pb$, and $^{212}Pb$. Moreover, these radioisotopes can also require chelators that are specific for their action. For example, in accordance with an embodiment, a CMP or CCMP which is labeled with $^{89}Zr$, would require a desferrioxamine chelator. Thus, included in the scope of the present invention includes CMPs having these isotopes and their respective chelators, uni- and bi-functional, where applicable, such as DTPA, DOTA, desferrioxamine, etc., that are known to those of ordinary skill in the art.

By "disease" is meant any condition or disorder that damages or interferes with the normal function of a cell, tissue, or organ. Examples of such diseases include: fibrosis, atherosclerosis, coronary artery disease, inflammatory diseases such as rheumatoid arthritis, infectious diseases, amyloidosis, idiopathic or congenital diseases of collagen such as Ehlers-Danlos syndrome or Marfan's syndrome, collagen vascular disease, cancers or other neoplasias.

By "an effective amount" is meant the amount required to identify, diagnose, image, or ameliorate the symptoms of a disease relative in an untreated or treated patient. The effective amount of active compound(s) used to practice the present invention for therapeutic treatment of a neurodegenerative disease varies depending upon the manner of administration, the age, body weight, and general health of the subject. Ultimately, the attending physician or veterinarian will decide the appropriate amount and dosage regimen. Such amount is referred to as an "effective" amount.

Non-limiting examples of biologically active agents include following: anabolic agents, androgenic steroids, anti-angiogenic compounds, anti-cancer compounds, anti-allergenic materials, anti-cholesterolemic and anti-lipid agents, anti-coagulants, anti-convulsants, anti-hypertensive agents, anti-infective agents, anti-inflammatory agents such as steroids, non-steroidal anti-inflammatory agents, anti-malarials, anti-nauseants, anti-neoplastic agents, anti-pyretic and analgesic agents, anti-spasmodic agents, anti-thrombotic agents, biologicals, cardioactive agents, cerebral dilators, coronary dilators, decongestants, diuretics, diagnostic agents, erythropoietic agents, mitotics, mucolytic agents, growth factors, neuromuscular drugs, nutritional substances, peripheral vasodilators, progestational agents, prostaglandins, vitamins, and prodrugs.

Still further, the following listing of peptides, proteins, and other large molecules may also be used, such as interleukins 1 through 18, including mutants and analogues; interferons a, y, and which may be useful for cartilage regeneration, hormone releasing hormone (LHRH) and analogues, gonadotropin releasing hormone transforming growth factor (TGF); fibroblast growth factor (FGF); tumor necrosis factor-α); nerve growth factor (NGF); growth hormone releasing factor (GHRF), epidermal growth factor (EGF), connective tissue activated osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-a-y-globulin; superoxide dismutase (SOD); and complement factors, and biologically active analogs, fragments, and derivatives of such factors, for example, growth factors.

The compositions can take the form of solutions, suspensions, emulsions, powders, sustained-release formulations, depots and the like. Examples of suitable carriers are described in "Remington's Pharmaceutical Sciences," Martin. Such compositions will contain an effective amount of the biopolymer of interest, preferably in purified form, together with a suitable amount of carrier so as to provide the form for proper administration to the patient. As known in the art, the formulation will be constructed to suit the mode of administration.

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

In vitro uses for CMP and caged CMP. Western blot and immunohistochemistry are the two most common techniques for detecting collagens, where a particular type of collagen is identified by antibody binding. However, because the triple helical domains which constitute the major part of the fibrous collagen (type I and II) have a highly repetitive triplet amino acid sequence (Gly-X-Y) and a tight rod-like structure, it is difficult to generate antibodies with high specificities against fibrous collagens. Therefore, extensive purification and selection steps, which involve multiple immunoaffinity purification against serum proteins and other non-collagenous ECM proteins, are needed to create collagen antibodies with low levels of cross-affinity. For antibodies that recognize the intact triple helical collagen epitopes, their affinity decreases dramatically when they are used in western blot and in formalin-fixed and/or paraffin embedded tissue samples because collagens in those samples are partially denatured. Moreover, antibody detection usually requires overnight reactions and additional detection steps involving secondary antibodies labeled with either a reporter enzyme or a fluorescent dye, which are often tedious and time-consuming. Considering these limitations, the present inventors sought to develop a broad-spectrum collagen staining agent that is easy to use and can bind not only to native collagens but also to denatured fibrous collagens.

Mixtures of proteins can be separated into individual components by various means, including electrophoresis and chromatography. Separation according to differences in mass can be achieved by electrophoresing in a polyacrylamide gel under denaturing conditions. One-dimensional and two-dimensional gel electrophoresis have become standard tools for studying proteins. One-dimensional SDS (sodium dodecyl sulfate) electrophoresis through a cylindrical or slab gel reveals only the major proteins present in a sample tested. Two-dimensional polyacrylamide gel electrophoresis (2D PAGE), which separates proteins by isoelectric focusing, i.e., by charge in one dimension and by size in the second dimension, is the more sensitive method of separation and will provide resolution of most of the proteins in a sample.

The proteins migrate in one- or two-dimensional gels as bands or spots, respectively. The separated proteins are visualized by a variety of methods; by staining with a protein specific dye, by protein mediated silver precipitation, autoradiographic detection of radioactively labeled protein, and by covalent attachment of fluorescent compounds. The latter method has been heretofore only able to be performed after the isoelectric focusing step of 2D PAGE. Immediately following the electrophoresis, the resulting gel patterns may be visualized by eye, photographically or by electronic image capture, for example, by using a cooled charge-coupled device (CCD).

To compare samples of proteins from different sources, such as different cells or different stages of cell development by conventional methods, each different sample is presently run on separate lanes of a one-dimensional gel or separate two-dimensional gels. Comparison is by visual examination or electronic imaging, for example, by computer-aided image analysis of digitized one or two-dimensional gels.

In accordance with one or more embodiments, the methods of the present invention can be used to identify collagen and collagen like protein fragments in any commonly used protein separation substrate, and any known separation technique. For example, the proteins are mixed and separated in the same medium by any suitable known separation technique, such as electrophoresis or chromatography. Electrophoresis techniques include one or two-dimensional electrophoresis, capillary zone electrophoresis, capillary gel electrophoresis, isoelectric focussing, isotacophoresis, and micellar electrokinetic chromatography. Chromatographic techniques include affinity chromatography, size exclusion chromatography, reverse phase chromatography, hydrophobic interaction chromatography and ion exchange chromatography.

The gels used in the methods and compositions of the present invention can be analyzed by a two-wavelength fluorescence scanner, by a fluorescent microscope or by any known means for detecting fluorescence. Gel analysis can be completely automated by means of computer-aided identification of protein differences. Using an electronic detection system such as a laser scanning system with a photo multiplier tube or a charged-coupled device (CCD) camera and a fluorescent light source.

In accordance with an embodiment, the present invention provides a method for detection of collagen or a protein having a collagen like domain in a substrate comprising: a) contacting the substrate with an effective amount of a solution comprising the collagen mimetic peptide or a collagen mimetic peptide conjugate described above, wherein the solution is pre-heated to a temperature above the melting point of the collagen mimetic peptide; b) allowing the collagen mimetic peptide, or conjugate sufficient time to bind collagen and/or gelatin in the substrate at a temperature below the melting point of the collagen mimetic peptide; and c) detecting the collagen mimetic peptide, or conjugate in the substrate.

As used herein, the term "substrate" denotes any known substrates useful in the separation of proteins from a mixture or cell lysate, for example. Common substrates include agarose and other acrylamides gels, used for example, in SDS-PAGE methods. In one or more alternate embodiments, substrates can include chromatography substrates such as, for example, affinity column, HPLC, and size exclusion purification substrates.

In accordance with an alternative embodiment, the term "substrate" means a tissue sample which has been fixed using commonly known methods for immunohistochemistry and related procedures, for example, paraffin or epoxy (polymer) imbedded tissues further treated with glutaraldehyde or other crosslinking agents known in the art.

In accordance with the methods of the present invention, one or more protein samples can be subjected to SDS-PAGE or similar procedures. Once the separation procedure is completed, the substrate or gel containing the separated proteins is placed in contact with a solution which contains a quantity of the CMP. The concentration of CMP can vary, but can be as low as about 1 µM to about 100 µM, including, for example, 5 µM, 10 µM, 20 µM, 40 µM, 50 µM, 60 µM, 80 µM and 90 µM. The solution is heated prior to contact with the substrate to a temperature which is higher than the melting point of the CMP, which varies from about 45° C. to 75° C., and then allowed to cool to room temperature and maintain contact with the substrate for a period of between about 0.5 hours to about 5 hours. The substrate is then washed and rinsed with a general buffer and the gel is then observed using a fluorescence detector or imaging device, for example, a Typhoon 9410 Variable Mode Imager (gmi-inc.com/molecular-dynamics-typhoon-9410-molecular-imager.html). The collagen and collagen like protein domains will bind the CMP and fluoresce at the appropriate excitation wavelength and show up as highlighted bands on the substrate.

In accordance with one or more embodiments, the present invention provides collagen-specific staining methods using simple CMPs conjugated to common fluorophores (e.g. carboxyfluoroscene), which allow direct detection of collagens and collagen-like proteins in protein separation substrates, such as SDS-PAGE, and in various mammalian tissue sections. By directly staining SDS-PAGE gels with fluorescently labeled CMPs, both intact (type I, II, and IV) and MMP-1 cleaved collagen (type I) chains as well as complement factor C1q were detected. Collagen bands containing as little as 5 ng were optically visualized while no staining was observed for fibronectin, laminin, and a collection of proteins from mammalian cell lysate. The CMP was unable to stain collagen-like bacterial protein which contains numerous charged amino acids that are believed to stabilize triple helix in place of Hyp.

In accordance with another embodiment, the present invention provides fluorescently labeled CMPs which can specifically visualize collagens in fixed tissue sections (e.g., skin, cornea, and bone) more effectively than anti-collagen I antibody, and allow facile identification of pathologic conditions in fibrotic liver tissues.

While western blot is useful for molecular level detection and quantification of collagens, direct visualization of collagens can help us identify the location of collagens in tissue samples and the pathological state of the diseased tissues with abnormal collagen remodeling activity. In immunohistochemistry, harvested tissues are often preserved by fixation, followed by cryosectioning and probing by different antibodies to determine the location of biomolecules. The fixation step is needed to keep the cellular components and overall tissue morphology from deterioration during histological study and long term storage; however the fixing procedures, which often include heat (microwave), and treatment with organic solvents (e.g. acetone and alcohols) and crosslinking reagents (e.g. paraformaldehyde), can denature the collagen molecules. Although such denaturation can reduce the number of epitopes for antibody binding, it could have an opposite effect on CMP probes. The denaturation may increase the number of binding sites for the CMP probes because the CMP preferentially hybridizes with denatured collagen strands over intact collagen fibers. For this reason, we anticipated that the fluorescent CMP probes could be an ideal collagen staining agent for histology. Since addition of heat activated peptide probes to tissue sections could result in further tissue damage and destruction of other heat sensitive antibodies (for co-staining), the caged CMP that can be activated by UV light was used for staining tissue sections.

In accordance with a further embodiment, the present invention provides a method for detection of collagen or a protein having a collagen like domain in a substrate comprising: a) contacting the substrate with an effective amount of a solution comprising the caged collagen mimetic peptide or a caged collagen mimetic peptide conjugate as described above; b) exposing the substrate in the solution of a) to UV light for sufficient time to caged collagen mimetic peptide or conjugate to be activated; c) allowing the activated collagen mimetic peptide, or conjugate sufficient time to bind collagen and/or gelatin in the substrate; and c) detecting the collagen mimetic peptide, or conjugate in the substrate.

In general, fixation is usually the first stage in a multistep process to prepare a sample of biological material for microscopy or other analysis. Therefore, the choice of fixative and fixation protocol may depend on the additional processing steps and final analyses that are planned. For example, immunohistochemistry uses antibodies that bind to a specific protein target. Prolonged fixation can chemically mask these targets and prevent antibody binding. In these cases, a 'quick fix' method using cold formalin for around 24 hours is typically used. In accordance with one or more embodiments, any fixation methods suitable for use in immunohistochemistry can be used.

The invention now being generally described, it will be more readily understood by reference to the following examples which are included merely for purposes of illustration of certain aspects and embodiments of the present invention, and are not intended to limit the invention. Further information related to CMPs can be found, e.g., in U.S. Patent Application Publication No. 2008/0287342, which is incorporated by reference herein as if set forth in its entirety.

EXAMPLES

In Vivo Materials and Methods

Peptide synthesis. Fmoc(N-o-nitrobenzyl)Gly-OH was synthesized as described in (*FEBS Lett.*, 525:20-24 (2002)) (FIG. 6A). Caged CMPs were coupled using standard solid-phase Fmoc and HBTU chemistry, with the exception of the amino acid following NBGly, which was conjugated by 9 molar equiv of the amino acid, 8.8 molar equiv of PyBroP, and 20 molar equiv of DIPEA for 24 hr. The peptides were purified by reverse phase HPLC and analyzed by MALDI-ToF (Table 1) and circular dichroism spectroscopy.

TABLE 1

Sequence and MALDI-ToF MS of collagen mimetic peptides (CMPs). CF, 5(6)-carboxyfluorescein; O, hydroxyproline; NB, nitrobenzyl; Ac, acetyl; C, cysteine; Ahx, aminohexanoic acid (As used herein, $^{NB}$Gly is a variant of $^{Pl}$Gly where the photolabile protecting group is -o-nitrobenzyl).

| CMP | Sequence | | | m/z calculated | m/z found |
|---|---|---|---|---|---|
| $CF^{NB}(GPO)_9$ | CF-GGG-(GPO)$_4^{NB}$GPO(GPO)$_4$ | before UV | [M + Na$^+$] | 3110.2 | 3109.4 |
| | | after UV | [M + Na$^+$] | 2975.1 | 2974.1 |
| $CF^{NB}(GPP)_9$ | CF-GGG-(GPP)$_4^{NB}$GPP(GPP)$_4$ | before UV | [M + Na$^+$] | 2966.2 | 2966.6 |
| | | after UV | [M + Na$^+$] | 2831.1 | 2831.3 |
| $CF^{NB}(G^DP^DP)_9$ | CF-GGG-(G$^D$P$^D$P)$_4^{NB}$G$^D$P$^D$P(G$^D$P$^D$P)$_4$ | before UV | [M + Na$^+$] | 2966.2 | 2966.3 |
| | | after UV | [M + Na$^+$] | 2831.1 | 2830.9 |
| $CF(GPO)_9$ | CF-GGG-(GPO)$_9$ | | [M + Na$^+$] | 2975.1 | 2975.4 |
| $CF(GPP)_9$ | CF-GGG-(GPP)$_9$ | | [M + Na$^+$] | 2831.1 | 2831.0 |
| $CF(G^DP^DP)_9$ | CF-GGG-(G$^D$P$^D$P)$_9$ | | [M + Na$^+$] | 2831.1 | 2831.1 |

TABLE 1-continued

Sequence and MALDI-ToF MS of collagen mimetic peptides (CMPs).
CF, 5(6)-carboxyfluorescein; O, hydroxyproline; NB, nitrobenzyl; Ac, acetyl;
C, cysteine; Ahx, aminohexanoic acid (As used herein, $^{NB}$Gly is a variant
of $^{Pl}$Gly where the photolabile protecting group is -o-nitrobenzyl).

| CMP | Sequence | | m/z calculated | m/z found |
|---|---|---|---|---|
| CF $^S$G$_9$P$_9$O$_9$ | CF-GGG-PGOGPGPOPOGOGOPPGOOPGGOOPPG | [M + Na$^+$] | 2975.1 | 2973.6 |
| Cys-Ahx-$^{NB}$(GPO)$_9$ | Ac-C-Ahx-(GPO)$_4$$^{NB}$GPO(GPO)$_4$ | [M + Na$^+$] | 2839.1 | 2837.8 |
| Cys-Ahx-$^S$G$_9$P$_9$O$_9$ | Ac-C-Ahx-PGOGPGPOPOGOGOPPGOOPGGOOPPG | [M + Na$^+$] | 2704.0 | 2703.6 |

Figure 6:
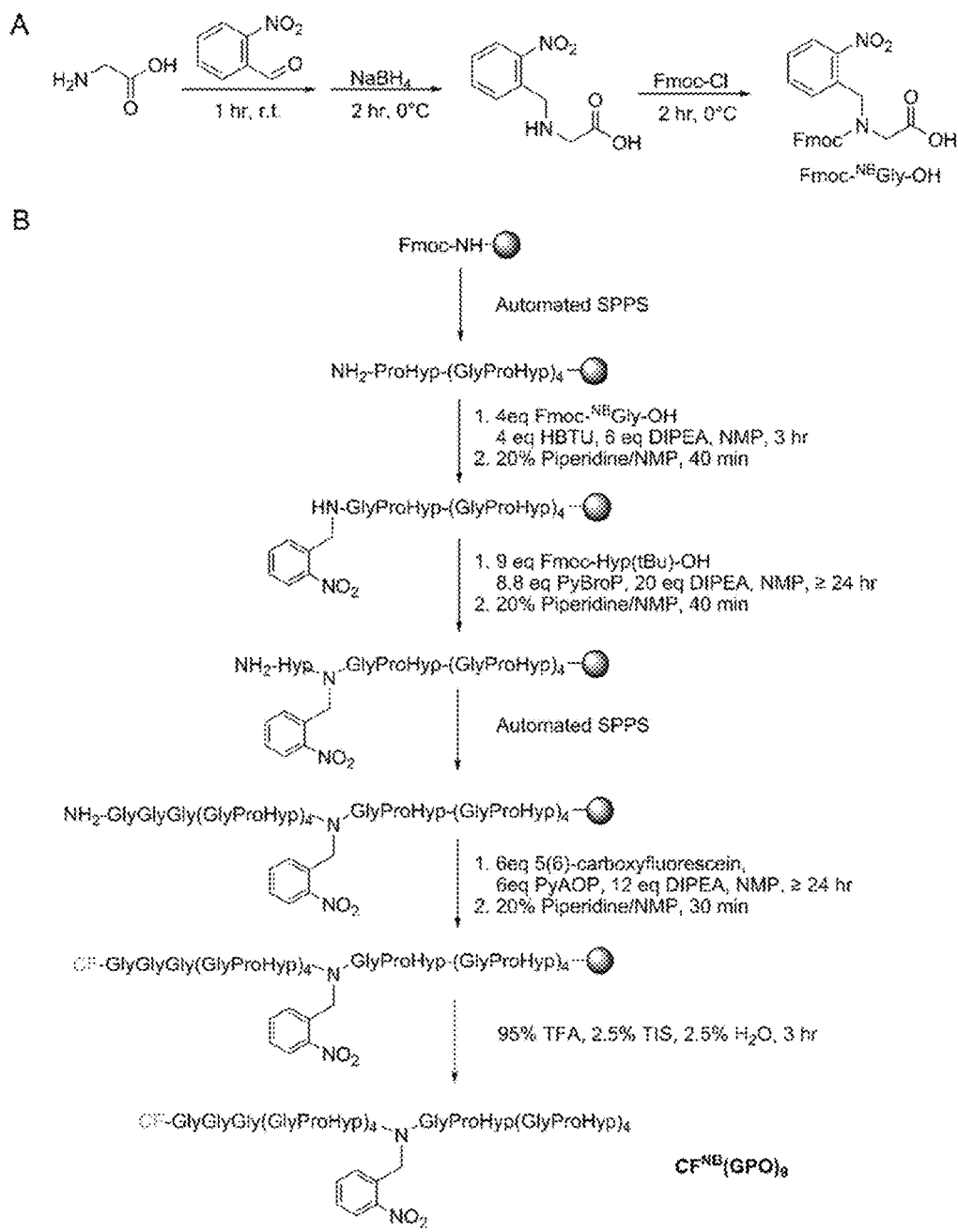
FIG. 6 depicts the synthesis of CF$^{NB}$(GPO)$_9$ (SEQ ID NO: 4). (A) Fmoc(N-o-nitrobenzyl)Gly-OH was synthesized according to Tatsu et al. with slight modifications: when conjugating Fmoc group onto N-2'-nitrobenzyl-glycine, a solution of 1.05 equivalent (1.94 g, 7.5 mmol) of fluorenylmethyloxy chloroformate (Fmoc-Cl) in 10 mL of acetone was added in a drop-wise fashion over 30 minutes to N-2'-nitrobenzyl-glycine (1 eq, 1.50 g, 7.14 mmol) dissolved in a mixture of 67 mL 3% NaHCO$_3$ and 53.6 mL of acetone vigorously stirring in an ice bath. The reaction mixture was stirred for another 1.5 hours followed by work-up as reported (*Collagen*, eds., Brinckmann J, Notbohm H, Müller P K (Springer, Verlag Berlin Heidelberg), pp 7-33 (2005)), producing 2.24 g (yield: 73%) of final product. (B) Combined automated and manual solid phase synthesis of CF$^{NB}$(GPO)$_9$ (SEQ ID NO: 4). Fluorescent tag, 5(6)-carboxyfluorescein was conjugated to the N-terminus of the peptide on resin using PyAOP and DIPEA followed by piperidine treatment.

Synthesis of caged CMPs (CCMPs). Non-caged peptides were synthesized on a 433A peptide synthesizer (Applied Biosystems) using standard Fmoc and HBTU chemistry. The caged peptides (0.1 mmol scale) were prepared using combined automated and manual solid phase synthesis (FIG. 6). Fmoc(N-o-nitrobenzyl)Gly-OH was synthesized following the modified method of Tatsu et al. (*FEBS Lett* 525:20-24. (2002)) (FIG. 6A). The peptide sequence preceding $^{NB}$Gly was synthesized automatically and Fmoc-$^{NB}$Gly-OH (4 molar equiv) was coupled manually by standard HBTU chemistry. The next amino acid (Fmoc-Hyp(tBu)-OH or Fmoc-$^{L/D}$Pro-OH) was coupled by PyBroP activation: 9 molar equivalent of the amino acid, 8.8 molar equivalent of PyBroP, 20 molar equivalent of DIPEA were added and allowed to react over 24 hours. The coupling efficiency was over 85% as estimated by HPLC. The remaining sequence was completed by automated synthesis, followed by on-resin labeling with 6 molar equivalent of 5(6)-carboxyfluorescein (Sigma) activated by 6 molar equivalent of PyAOP (Sigma) (*Anal Biochem* 424:137-139 (2012)). Resins were treated with trifluoroacetic acid (TFA)/triisopropylsilane (TIS)/water (95:2.5:2.5) for 3 hr and the target peptide was precipitated by adding excess cold ether to the TFA solution. Crude peptide products were purified by reverse phase HPLC on a Vydac C18 column using a linear gradient (5-45% B in 40 minutes) mixture of water (A, 0.1% TFA) and acetonitrile (B, 0.1% TFA). Purified peptides were analyzed by Bruker AutoFlexIII MALDI-ToF (Bruker Daltonics; Table 1).

Circular dichroism spectroscopy. CD spectra were collected on JASCO 715 spectrophotometer equipped with a JASCO PTC-348 WI temperature controller and quartz cells (0.1 mm path length). CMP solutions (320 μL, 150 μM in 1×PBS) were stored at 4° C. for at least 24 hours before measurement. For photo-decaging, samples were exposed to 365 nm UV light for at least 30 minutes before the 4° C. incubation. The thermal melting studies were performed by measuring the ellipticity at 225 nm with 60° C./hr heating rate. Raw CD signal was normalized to mean residue ellipticity based on the peptide's length and concentration (*Biopolymers* 95:94-104 (2011)). Melting temperatures ($T_m$) were determined by fitting the mean residue ellipticity to a two-state model (*Org Lett* 8:4735-4738 (2006)). To measure the refolding kinetics, CMP solution was thermally denatured at 75° C. for 10 minutes in a cuvette and rapidly quenched to 25° C. in an ice-water bath, after which the CD signal at 225 nm was observed over time at 25° C. The CD spectra of intact and MMP-1 cleaved type I collagen (FIG. 12) was measured in 90 μg/mL protein solutions in 20 mM acetic acid buffer at 22° C. The 37° C. thermal stability profile (FIG. 2E, inset) was generated by monitoring the ellipticity at 222 nm immediately after transferring the cuvette to a temperature controlled cuvette holder pre-set to 37° C. The $T_m$ values reported in this study are approximately 10° C. higher than the equilibrium $T_m$ due to high heating rate (60° C./hr) (*Biopolymers* 73:682-688 (2004)).

Collagen/gelatin binding assays. Collagen solution (200 μL, 3.71 mg/mL, type I rat tail, BD Science) in 0.02 N acetic acid was added to each well of a 96-well black/clear-bottom plate (Costar) and air-dried. To make gelatin films, the same collagen solution was denatured at 70° C. for 15 minutes before applying to the well. The dried films were neutralized and washed with 1×PBS buffer (pH 7.4) and deionized water. PBS solution of carboxyfluorescein-labeled caged CMP (40 μL, 50 μM, unless indicated otherwise) pre-equilibrated at 4° C. was added onto each reconstituted collagen or gelatin film and exposed to 365 nm UV light (10 mW/cm$^2$, from mercury arc lamp) for 11 minutes on ice. Wells for the UV-negative control groups were covered with aluminum foil to block UV exposure. After incubation at 4° C. for over 3 hours (unless indicated otherwise), the unbound materials were removed by rinsing with PBS buffer and deionized water. The films were allowed to dry in dark, after which the fluorescence (ex: 489 nm, em: 533 nm) was measured with a SpectraMax Gemini XPS microplate reader (Molecular Devices). Each binding experiment was done in triplicate.

Quantification of CF(GPO)$_9$ (SEQ ID NO: 10) bound on type I collagen films. Following photo-induced binding, CMP-bound collagen films (e.g. the UV+ group of FIG. 10A) were digested with 200 μL of collagenase (Sigma, C0130) solutions (1 mg/mL) in TESCA buffer (50 mM TES buffer with 1.36 mM CaCl$_2$, pH 7.4) for 1 hr at 37° C. The digested solutions were directly used for fluorescence measurement (ex: 489 nm, em: 533 nm). For the standard curve, a series of solutions containing known amounts of CF$^{NB}$(GPO)$_9$ (SEQ ID NO: 4) (0 to 0.35 nmol) were applied to blank collagen films and air-dried, followed by collagenase digestion and fluorescence measurement as described above. The amount of bound CF(GPO)$_9$ (SEQ ID NO: 10) was determined by comparing the fluorescence intensity of the digested collagen/CMP solutions with the standard curve, and the binding density was determined by dividing the amount bound by the area of the well. The experiment was performed in triplicate.

CMP binding assay on thermally-denatured type I and II collagens. A solid-state protein coating instead of a reconstituted gelatin film (as described above) was chosen as the binding substrate to avoid the collagen type dependent film instability. Wells of nunc black 96-well maxisorp plate (Thermo Scientific) were charged with 50 μL of 1×PBS buffer containing 100 μg/mL type I or type II (bovine, BD Science) collagen which was denatured by 10 minutes of incubation at 75° C. After 1 hour, the coating solutions were removed and wells were washed with 1×PBS buffer containing 1 mg/mL BSA (PBSB), and blocked with 50 mg/mL BSA in PBS for 1 hour, followed by additional wash with PBSB. $CF^{NB}(GPO)_9$ (SEQ ID NO: 4) or $CF^{S}G_9P_9O_9$ (SEQ ID NO: 5) solution (20 μM, 50 μL in PBS) was added to each well, exposed to UV light for 10 min, and incubated at room temperature for 2.5 hours. Wells were washed three times with 100 μL of PBSB followed by fluorescence (ex: 489 nm, em: 533 nm) reading with a SpectraMax M-2 microplate reader (Molecular Devices). Each binding experiment was done in triplicate. The background fluorescence of empty wells was subtracted from the raw fluorescence data.

Photo-patterning of collagen and gelatin films. On the lid of a 48-well cell culture plate (Costar), 150 μL of type I collagen solution (3.71 mg/mL) was evenly applied and enclosed with a condensation ring (diameter: 11 mm). The solution was allowed to dry and washed three times with PBS to form a collagen film. Gelatin films were made in the same way using denatured type I collagen which was pre-incubated at 70° C. for 15 minutes. $CF^{NB}(GPO)_9$ (SEQ ID NO: 4) solution (100 μL, 200 μM in 1×PBS) was applied to each film and incubated at room temperature for 20 min. Excess CMP solution was removed, leaving collagen/gelatin films swollen in $CF^{NB}(GPO)_9$ (SEQ ID NO: 4). A transparency mask was carefully mounted on top of the condensation ring and the films were exposed to UV light (365 nm) through the transparency mask for 12 minutes at 4° C., followed by 1 hour incubation to allow peptide binding. The films were washed with deionized water and imaged by Gel Doc EQ system (BioRad).

Figure 12:
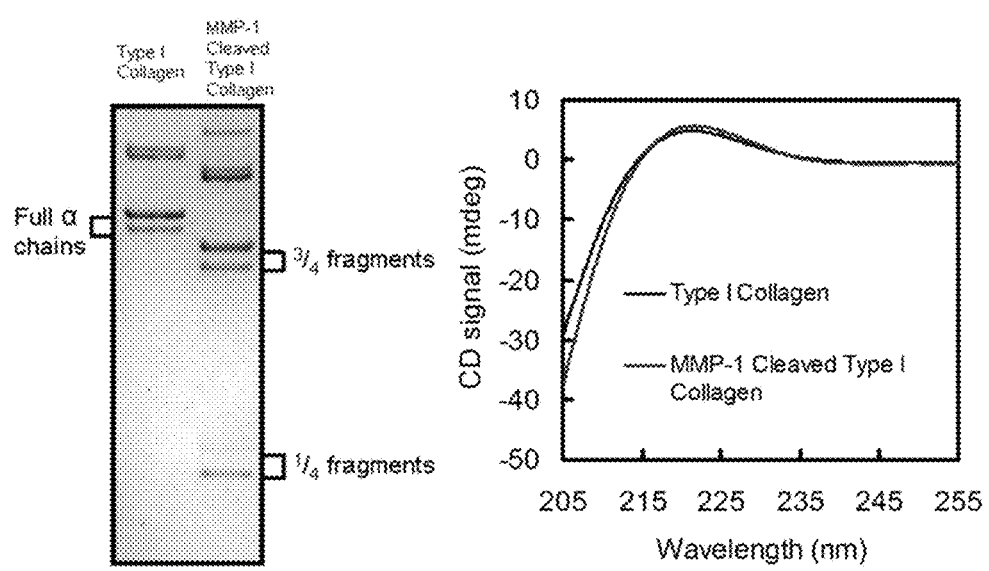
FIG. 12 depicts the characterization of MMP-1 cleaved type I collagen. Left: SDS-PAGE and coomassie brilliant blue staining of MMP-1 cleaved collagen, showing the ¾ and ¼ fragments and no residual full length α chains, indicating almost complete digestion. Right: CD spectra of collagen and MMP-1 cleaved collagen (90 μg/mL) in 20 mM acetic acid buffer at 22° C. displaying their similar triple helical contents.
Figure 13:
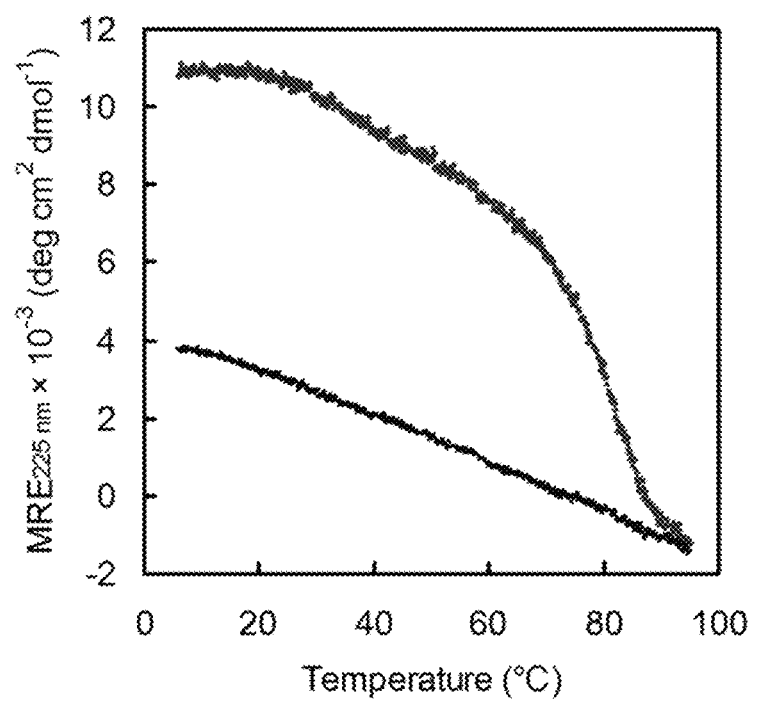
FIG. 13 shows CD thermal melting curves of photo-decaged IR-Ahx-NB(GPO)$_9$ (SEQ ID NO: 7) (red) and IR-Ahx-SG9P9O9 (SEQ ID NO: 8) (blue, scrambled sequence). IR-Ahx-SG9P9O9 (SEQ ID NO: 8) exhibited no triple helix forming capacity, while IR-Ahx-NB(GPO)$_9$ (SEQ ID NO: 7) demonstrated the expected folding propensity, forming CMP homotrimer with Tm above 75° C. after decaging. All samples were incubated at 4° C. for at least 24 hr before CD measurement to ensure folding.

MMP-1 digestion of type I collagen and CMP binding assays. ProMMP-1 (1 μg, EMD Millipore) was activated by p-aminophenylmercuric acetate (1.1 mM) in 132.5 μL of TNC buffer (50 mM Tris-HCl, 0.15 M NaCl, 5 mM $CaCl_2$, 0.02% $NaN_3$, pH 7.5) at 37° C. for 3 hr. Type I collagen (62.6 μg) was subsequently added to the MMP-1 solution and incubated at room temperature for at least 3 days. Digested products were analyzed by SDS-PAGE and circular dichroism spectroscopy (FIG. 12). Wells of nunc black 96-well maxisorp plate were charged with 50 μL of TNC buffer containing 0.5 M glycerol, and 100 μg/mL collagen or MMP-1 cleaved collagen, and incubated at room temperature. The collagen solutions used were either kept at room temperature (22° C.) or incubated at 37° C. for 1 minute just prior to coating. After 2.5 hours, the coating solutions were removed and wells were washed with PBSB (1 mg/mL BSA in 1×PBS) and blocked with 50 mg/mL BSA in PBS for 1 hr, followed by additional wash with PBSB. $CF^{NB}(GPO)_9$ (SEQ ID NO: 4) solution (20 μM, 50 μL in PBS) was added to each well, exposed to UV light for 10 min, and incubated at room temperature for 2.5 hours. Wells were washed extensively with PBSB followed by fluorescence (ex: 489 nm, em: 533 nm) reading with a SpectraMax M-2 microplate reader (Molecular Devices). Each binding experiment was done in triplicate. The background fluorescence of empty wells was subtracted from the raw fluorescence data. For estimating the amount of adsorbed protein, un-blocked collagen-coated wells were treated with 100 μM 5-(4,6-dichlorotriazinyl)aminofluorescein (DTAF, 50 μL, in 0.1 M sodium borate buffer) at room temperature for 3 hours, and the fluorescence (ex: 489 nm, em: 533 nm) of the well was measured after washing with 1×PBS. For each collagen substrates, fluorescence from the CMP binding was normalized by the fluorescence from the DTAF staining to calculate the relative CMP binding level per protein.

Staining of SDS-PAGE gels using photo-decaged $CF(GPO)_9$ (SEQ ID NO: 10). MMP-1 digested type I collagen (3.5 μg) was separated by SDS-PAGE (4-12% polyacrylamide gel) under non-reducing condition, along with unstained protein ladder (Life technologies, LC5801). After washing, the gel was soaked in 6 μM $CF^{NB}(GPO)_9$ (SEQ ID NO: 4) (or $CF^{S}G_9P_9O_9$ (SEQ ID NO: 5)) in 1×PBS solution, followed by exposure to 365 nm UV light for 15 min, and 2.5 hr of staining. The gel was washed with deionized water and scanned using Typhoon 9410 Imager (GE Healthcare) with 488 nm fluorescence channel. Afterwards, the protein gel was stained by coomassie brilliant blue and imaged by Gel Doc EQ system (BioRad).

Labeling CMPs with near infrared fluorescent dyes. Caged Cys-Ahx-$^{NB}(GPO)_9$ (SEQ ID NO: 13) [C-Ahx-$(GPO)_4{}^{NB}GPO(GPO)_4$ (SEQ ID NO: 13)] and scrambled peptide Cys-Ahx-$^{S}G_9P_9O_9$ (SEQ ID NO: 14) (C-Ahx-PGOGPGPOPOGOGOPPGOOPGGOOPPG) (SEQ ID NO: 14) were synthesized using the SPPS protocol as described above. After the acetylation of the N-terminal amines, the peptides were cleaved from the resin with TFA/TIS/1,2-ethanedithiol/water (94:1:2.5:2.5). After HPLC purification (MADLI in Table 1), both peptides (~1.2 mg for each labeling reaction) were labeled with 0.25 mg of either IRDye 680RD maleimide or IRDye 800CW maleimide (LI-COR Biosciences) in 300 μL of 3×PBS buffer at 4° C. overnight and further purified by HPLC on a Vydac C18 column using a linear gradient (13-30% B in 34 min) mixture of water (A, 0.1% TFA) and acetonitrile (B, 0.1% TFA).

In vivo tumor targeting. All animal studies were undertaken in compliance with the regulations of the Johns Hopkins Animal Care and Use Committee. Both prostate-specific membrane antigen (PSMA) expressing (PC3-PIP) and non-PSMA expressing (PC3-flu) PC-3 prostate cancer cell lines were grown in RPMI 1640 medium (Invitrogen) containing 10% fetal bovine serum (FBS) and 1% Pen-Strep (Biofluids). Eight- to twelve-week-old male, non-obese diabetic (NOD)/severe-combined immunodeficient (SCID) mice (JHU Cancer Center) were implanted subcutaneously with PC3-PIP and PC3-flu cells (1×$10^6$ in 50 μL of HBS) behind the right and left forearms, respectively. Mice were used for in vivo tests when the xenografts reached 5-7 mm in diameter. Hair remover was applied to the entire ventral tumor region in both mice to enhance imaging. Saline solution (100 μL) containing 3.7 nmol of IR-Ahx-$^{NB}(GPO)_9$ (SEQ ID NO: 7) and 1 nmol of cysteine (for quenching photo cleaved aldehyde byproduct) sitting at approximately 40° C. was exposed to UV light (365 nm, >25 mW/$cm^2$) for 5 min and immediately injected to the mouse intravenously via the lateral tail vein. Control peptide IR-Ahx-$^{S}G_9P_9O_9$ (SEQ ID NO: 8) was injected into the second mouse following the identical procedure. Images, shown in rainbow format, were acquired at designated times using a Pearl Impulse Imager (LI-COR Biosciences) with fixed excitation (785 nm) and fluorescence emission wavelengths (800 nm). The same procedures were performed on another pair of NOD-SCID mice bearing two subcutaneous PC3-PIP tumors. One dose of MMPSense 680™ (2 nmol in 150 μL 1×PBS, PerkinElmer) was administered to each mouse via tail vein ~80 hours post CMP injection. After 22 hours (corresponding to 102 hours PI of CMP), the mice were imaged at both 710 nm (MMPSense) and 800 nm (CMP). The mice were sacrificed by cervical dislocation and their internal organs exposed to allow imaging of deep tissues.

Figure 15:
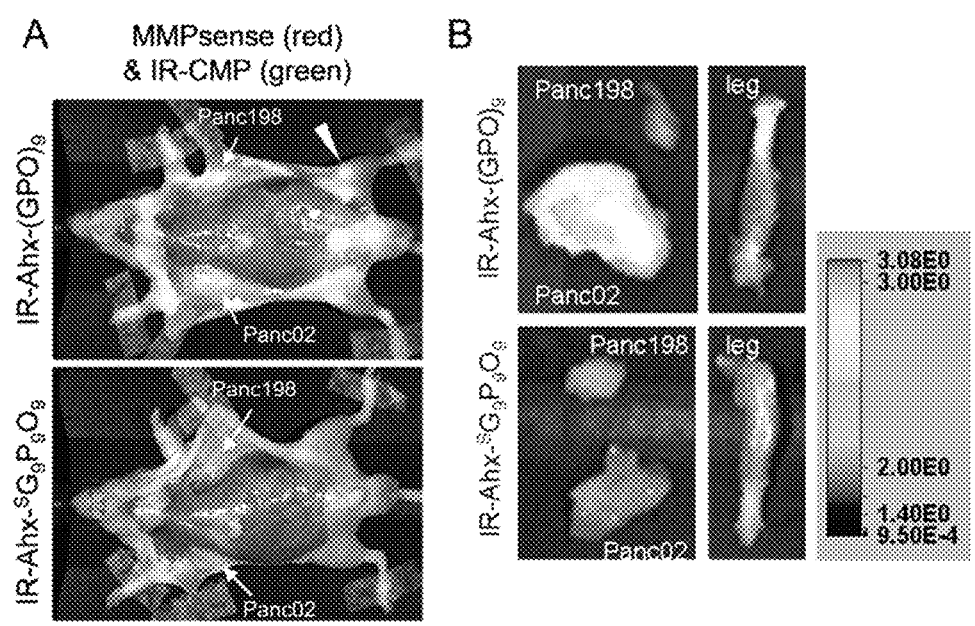
FIG. 15 shows NIRF images of pancreatic cancer tumors targeted by CMPs. A pair of athymic nu/nu mice bearing Panc02 (forward right flank) and Panc198 (forward left flank) tumors (arrows) were administered with approximately 4 nmol of photo-decaged IR-Ahx-$^{NB}$(GPO)$_9$ (SEQ ID NO: 7) or same amount of IR-Ahx-$^S$G$_9$P$_9$O$_9$ (SEQ ID NO: 8) via tail vein injection. (A) Ventral views of the mice after midline surgical laparotomy at 96 hr post CMP injection and 24 hours post MMPSense 680 injection, showing the co-localization (in yellow) of MMP activity (red) and CMP binding (green) in the tumors and surrounding tissues as well as the CMP uptake in the knee joint (arrow head). The mouse injected with IR-Ahx-$^S$G$_9$P$_9$O$_9$ (SEQ ID NO: 8) showed no peptide accumulation and only MMPSense signal is seen.

Murine Panc02 and human Panc198 cells were acquired from the ATCC (Rockville, Md.) and cultured in RPMI1640 supplemented with 10% FBS, 10 μg/mL of streptomycin and 10 I.U./mL of penicillin at 37° C. in 5% $CO_2$ and humidified air until 80-95% confluence. The cells were then trypsinized and formulated at either $2\times10^6$ cells/100 μL (Panc198) or $1\times10^6$ cells/100 μL (Panc02) followed by subcutaneous inoculation into 12-week-old female athymic nu/nu mice (NCI). Panc198 and Panc02 cells were inoculated subcutaneously behind the left and right shoulder, respectively. When the Panc02 xenograft reached 4-6 mm in diameter (~2 weeks after inoculation), each mouse was intravenously administered with solution containing 4 nmol of photoactivated IR-Ahx-$(GPO)_9$ (SEQ ID NO: 9) or IR-Ahx-$^SG_9P_9O_9$ (SEQ ID NO: 8) and 1 nmol of cysteine, followed by MMPsense injection and NIRF imaging as described. Both mice's Panc02 and Panc198 tumors as well as the legs which showed CMP uptake were harvested and imaged (FIG. 15).

In vivo skeleton targeting. PBS solution (100 μL) containing 4 nmol of IR'-Ahx-$^{NB}(GPO)_9$ (SEQ ID NO: 7) or IR'-Ahx-$^SG_9P_9O_9$ (SEQ ID NO: 8), and 1 nmol of cysteine equilibrated at 37° C. was exposed to UV light (365 nm, >25 mW/cm$^2$) for 5 minutes and immediately injected to a male BALB/c mouse (about 9 weeks old) via tail vein. One dose of IRDye800CW BoneTag™ (10 nmol, LI-COR Biosciences) was administered to each mouse via tail vein ~72 hours post CMP injection. After 24 hours (corresponding to 96 hr PI of CMP), the mice were sacrificed by cervical dislocation and their skins were removed to allow imaging of deep tissues. Major organs and the skeleton were harvested and imaged by a Pearl Impulse Imager at both 710 nm (CMP) and 800 nm (BoneTag).

Figure 17:
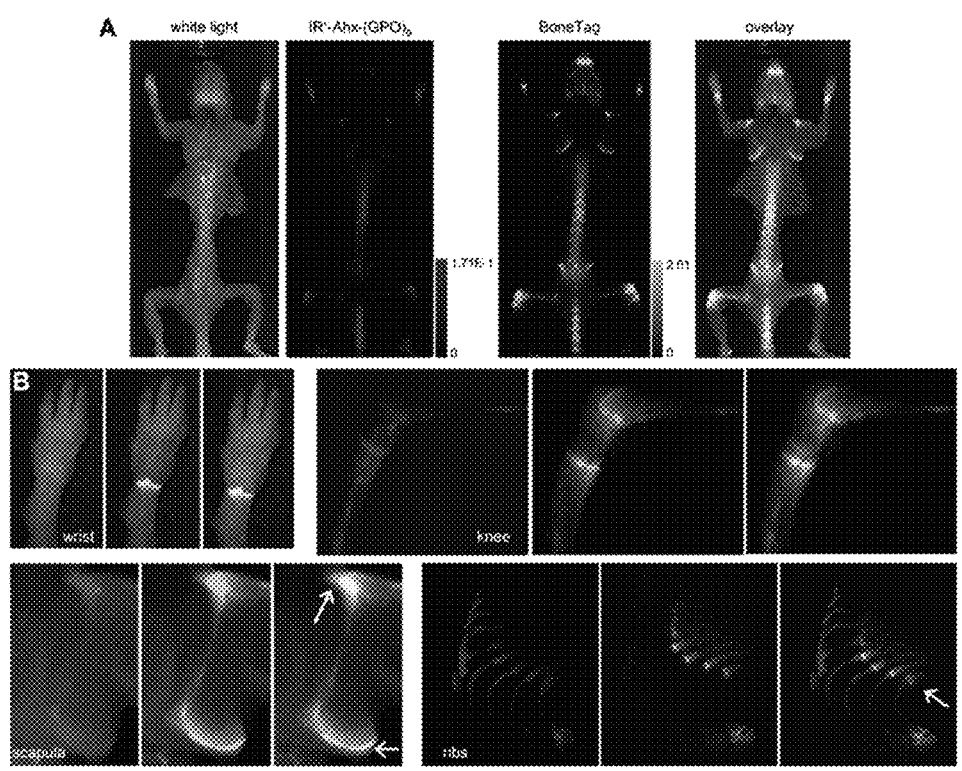
FIG. 17 depicts (A) white light and NIRF dorsal images of the same BLAB/c mouse shown in FIG. 4A,C and FIG. 16, after removing all non-skeletal tissues, demonstrating the similar overall distribution of IR'-Ahx-(GPO)$_9$ (SEQ ID NO: 9) (in red), and BoneTag (in green), especially in vertebral spine, knees, wrists, scapulae and maxilla (overlay in yellow). (B) High resolution images of separate fluorescence channels indicated that precise locations of these signals are slightly different for the two probes. In the wrist, BoneTag (green) highlights the epiphyseal line of radius and ulna, and CMP (red) shows radius and ulna (lower) and carpal and metacarpal bones. The knee is well defined by intense BoneTag uptake along mineralized bone and colocalizes with CMP at the endochondral junctions while CMP specific uptake can be seen in the articular cartilage and meniscus as well as focal regions within the tibia and the femur head. Details of the scapula views show CMP uptake in articular cartilage (white arrow) and lateral border cartilage (yellow arrow). The costochondral junction (arrow) within the ribs is clearly seen where mineralized bone ends (BoneTag) and cartilaginous ribs begin (CMP). The ribs and knee images were scanned using LI-COR Odyssey imager.

Ex vivo hind limb and right hemisphere of ribs were manually stripped of most skeletal muscle and scanned laterally using a LI-COR Odyssey imager set to 23 micron resolution in both the 710 nm (CMP) and 800 nm (BoneTag) channels. The resulting images were processed using the Odyssey software to generate single channel and merged images (FIG. 4C, FIG. 17B, ribs and knee).

Figure 4:
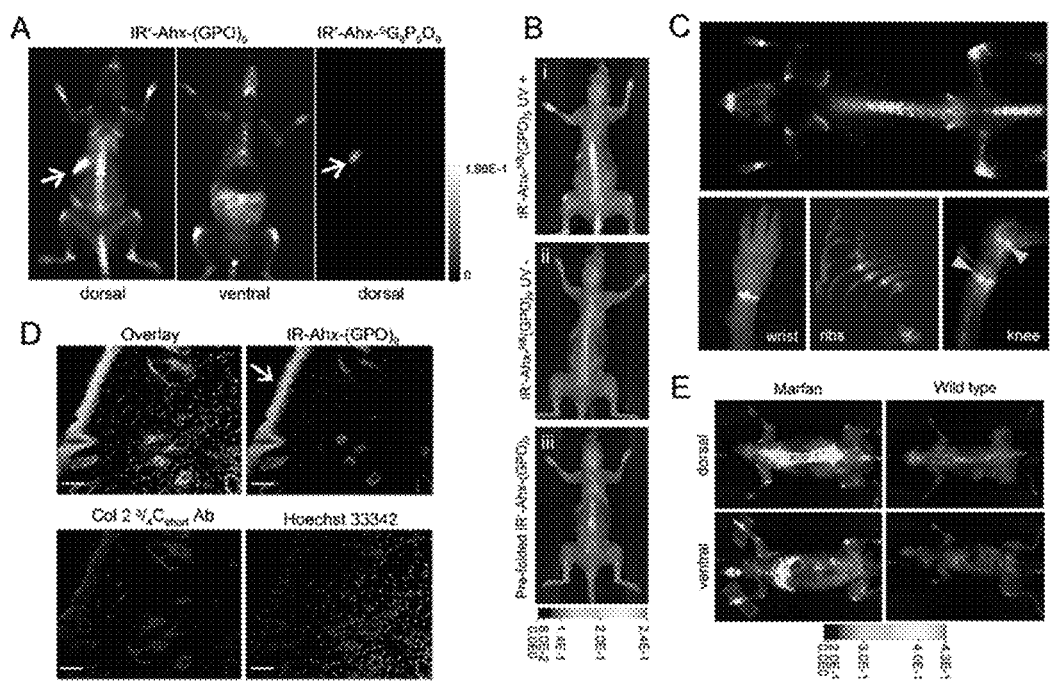
FIG. 4 shows in vivo targeting of collagen remodeling in bones and cartilages by CMP hybridization. (A) Whole body NIRF images of BLAB/c mice injected intravenously with photo-decaged IR'-Ahx-(GPO)$_9$ (SEQ ID NO: 9) or IR'-Ahx-$^S$G$_9$P$_9$O$_9$ (SEQ ID NO: 8) showing skeletal uptake of only the IR'-Ahx-(GPO)$_9$ (SEQ ID NO: 9) probes. Arrows show fluorescence from the chlorophyll in the digestive system. (B) Dorsal NIRF images of mice injected intravenously with photo-decaged IR'-Ahx-(GPO)$_9$ (SEQ ID NO: 9) (i), caged IR'-Ahx-NB(GPO)$_9$ (SEQ ID NO: 7) (ii), or pre-folded triple helical IR'-Ahx-(GPO)$_9$ (SEQ ID NO: 9) (iii). The absence of signal from mice ii and iii strongly suggests that the skeletal CMP uptake is due to its triple helical folding propensity. (C) Dual-NIRF image of the whole skeleton showing the overall uptake of IR'-Ahx-(GPO)9 (SEQ ID NO: 9) (red) and BoneTag™ (stains calcifying tissues in green) and corresponding high resolution images (colocalization shown in yellow). In the wrist, specific CMP uptake (red) is seen in carpal-metacarpal structures and BoneTag uptake is seen in epiphyseal line of radius and ulna; costochondral junctions within the ribs are visualized where mineralized bone ends (green-yellow) and cartilaginous ribs begin (red); CMPs co-localize with BoneTag™ at endochondral junctions (green arrowheads) in the knee while CMP-specific uptake can be seen within the articular cartilage and meniscus (red arrowhead) as well as focal regions within the tibia and the femur head. (D) Immunofluorescence micrographs of ex vivo knee cartilage sections subsequently stained with anti-Col 2¾Cshort antibody and Hoechst 33342 showing high CMP accumulation at the superficial zone of the cartilage (arrow, scale bars: 100 μm).

The same CMP injection and imaging procedure was performed in 12-month old Marfan mice, developed as reported (*J Clin Invest* 114:172-181 (2004)), as well as age- and gender-matched wild type littermates (FIG. 4E).

In vivo control peptide studies. IR'-Ahx-$^{NB}(GPO)_9$ (SEQ ID NO: 7) (4 nmol) and 1 nmol of cysteine in 100 μL of PBS was exposed to UV light for 5 minutes and immediately injected to CD1 nude mice via tail vein (FIG. 4B, panel i). Another mouse was injected with the same solution without the UV exposure (FIG. 4B, panel ii). For the third mouse, IR'-Ahx-$^{NB}(GPO)_9$ (SEQ ID NO: 7) was fully de-caged by UV and allowed to fold into triple helix at 4° C. for over 48 hr before injection (FIG. 4B, panel iii). The whole body scan was taken at 96 hours PI using a Pearl Impulse Imager after skin removal as previously described.

Ex vivo immunofluorescence histology of the tumors and the knee cartilage. PC-3 tumors were harvested and cryosectioned to 20 μm thickness on charged glass slides without any chemical fixation. The unfixed slides were probed with anti-CD31-PE antibody conjugate (Abcam, ab25644, 1:67) and anti-Col 2¾Cshort antibody (IBEX, 50-1035, 1:100) in 10% FBS (Sigma) in PBS for 1 hour at room temperature. The anti-collagen antibody was detected with a secondary anti-rabbit-AlexaFluor488 immunoconjugate (Invitrogen, A11070, 1:250). The slides were washed and covered with glass cover slips.

Legs of mice from in vivo PanC tumor targeting experiment (see above and FIG. 15) were harvested and frozen on dry ice following 96 hours NIRF imaging. The legs were stored at −80° C. until brief thawing and manual recovery of knee cartilage for subsequent cryosectioning. Cartilage specimens were sectioned to 15 μm thickness using an HM 550 cryotome and transferred onto charged glass microscope slides (VWR Superfrost). The sections were probed with rabbit anti-Col 2¾$C_{short}$ antibody (1:40) in 10% FBS in PBS for 1 hr at room temperature, followed by secondary anti-rabbit-AlexaFluor488 immunoconjugate (1:250) in PBS and 1 ng/mL of Hoecst 33342 dye (Fisher Scientific) in PBS, before washing and mounting. All images were recorded and processed using a Nikon 80i epifluorescence microscope with Nikon Imaging Software Elements. CMP images (800 nm) were acquired over a standardized 8 second exposure time.

In Vitro Materials and Methods.

For peptide synthesis and labeling, Fmoc-Gly-OH, Fmoc-Pro-OH, H-Gly-OH, fluorenylmethyloxy chloroformate (Fmoc-Cl) and synthesis reagents including HBTU, DIPEA, NMP and trifluoroacetic acid (TFA) were purchased from Advanced ChemTech (Louisville, Ky.) and used without further purification. Fmoc-Hyp(tBu)-OH and PyBroP were purchased from EMD millipore (San Diego, Calif.). Tenta-Gel R RAM resin was purchased from Peptides International (Louisville, Ky.). 5(6)-carboxytetramethylrhodamine (TAMRA) was purchased from Life Technologies (Carlsbad, Calif.). Piperidine, PyAOP, nitrobenzaldehyde, 5(6)-carboxyfluorescein (CF), triisopropylsilane (TIS) and all other chemicals were purchased from Sigma-Aldrich (St. Louis, Mo.) and used without further purification.

Acid soluble rat-tail type I collagen, bovine type II collagen, and mouse type IV collagen were purchased from BD Bioscience (San Jose, Calif.). Complement component C1q from human serum, fibronectin from bovine plasma, and laminin from Engelbreth-Holm-Swarm murine sarcoma basement membrane were purchased from Sigma-Aldrich. ProMMP-1, and p-aminophenylmercuric acetate were acquired from EMD millipore. Human umbilical vein endothelial cells (HUVECs) and EGM-2 cell growth media were obtained from Lonza (Walkersville, Md.). Precast NuPAGE® Novex 4-12% Bis-Tris Gel (1.0 mm, 12 well), Novex® Sharp unstained protein standard, and SDS-PAGE running buffer, sample buffer, and other SDS-PAGE reagents were purchased from Life Technologies.

To prepare MMP-1 cleaved collagen chain fragments, proMMP-1 (1 μg) was activated by p-aminophenylmercuric acetate (1.1 mM) in 132.5 μL of TNC buffer (50 mM Tris-HCl, 0.15 M NaCl, 5 mM $CaCl_2$, 0.02% $NaN_3$, pH 7.5) at 37° C. for 3 hr, after which type I collagen (62.6 μg) was added to the activated MMP-1 solution and incubated at room temperature for at least 3 days. To obtain the cell lysate, confluent HUVECs cultured in EGM-2 media at 37° C. were lysed with lysis buffer (25 mM Tris-HCl, 0.5% Triton X-100, 200 mM NaCl, 2 mM EDTA, phosphatase and protease inhibitors; Roche Applied Science). The lysate solution was spun at 15,000 g for 15 min and the supernatant was collected. The recombinant streptococcal collagen-like protein Scl2.28CL was expressed and characterized following the methods introduced by Mohs et al. (*J. Biol. Chem.* 282, 29757-29765 (2007)).

For immunohistochemical staining, anti-collagen I antibody was purchased from Abcam (ab292, Cambridge, Mass.); bovine serum albumin (BSA), goat serum, and Triton X-100 were purchased from Sigma-Aldrich; DAPI was obtained from Roche Applied Science (Indianapolis, Ind.); Alexa Fluor® 594 F(ab')$_2$ fragment of goat anti-rabbit IgG and Prolong® Gold antifade reagent were purchased from Life Technologies. The skin and cornea tissues were harvested from a 23 month-old wild-type C57BL/6 mouse. The tissues were fixed with 4% paraformaldehyde in PBS solution (pH 7.4) for 1 hour and cryopreserved in Tissue-Tek O.C.T. medium (Sakura Finetek, Torrance, Calif.). Cryosections of 8 μm thickness were obtained and mounted onto charged glass slides. Paraffin embedded mouse bone sections were a kind gift from Dr. Catherine Foss and Dr. Collin Torok at Johns Hopkins University School of Medicine. The leg containing the tibia bone was harvested from a 12-week-old female athymic nu/nu mouse. The muscle tissues were manually trimmed, and the bone was fixed in 10% neutral-buffered formalin at room temperature overnight. The bone was demineralized in Decal Stat solution (Decal Chemical, Suffern, N.Y.) for 3 hr at room temperature, embedded in paraffin and sectioned to 4 μm at Tissue Microarray Facility of Johns Hopkins University. The formalin-fixed normal and fibrotic rat livers were a kind gift from Jie Yan and Yuzhan Kang at National University of Singapore. The tissues were sectioned to 10 μm thickness on glass slides and stained by Masson trichrome by the Reference Histology Laboratory, Johns Hopkins Medical Institutions.

Figure 27C:
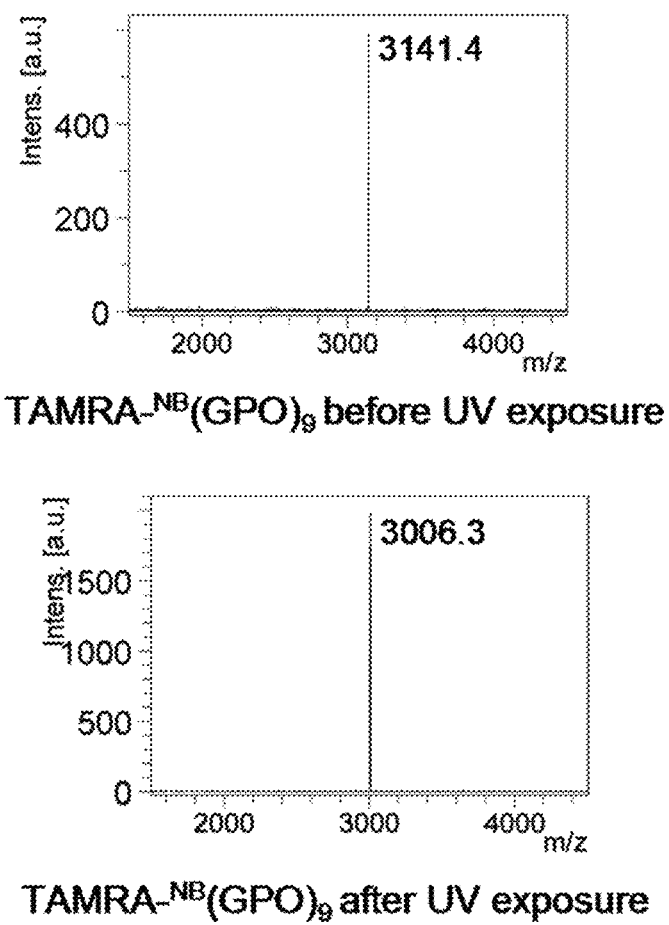
Figure 28:
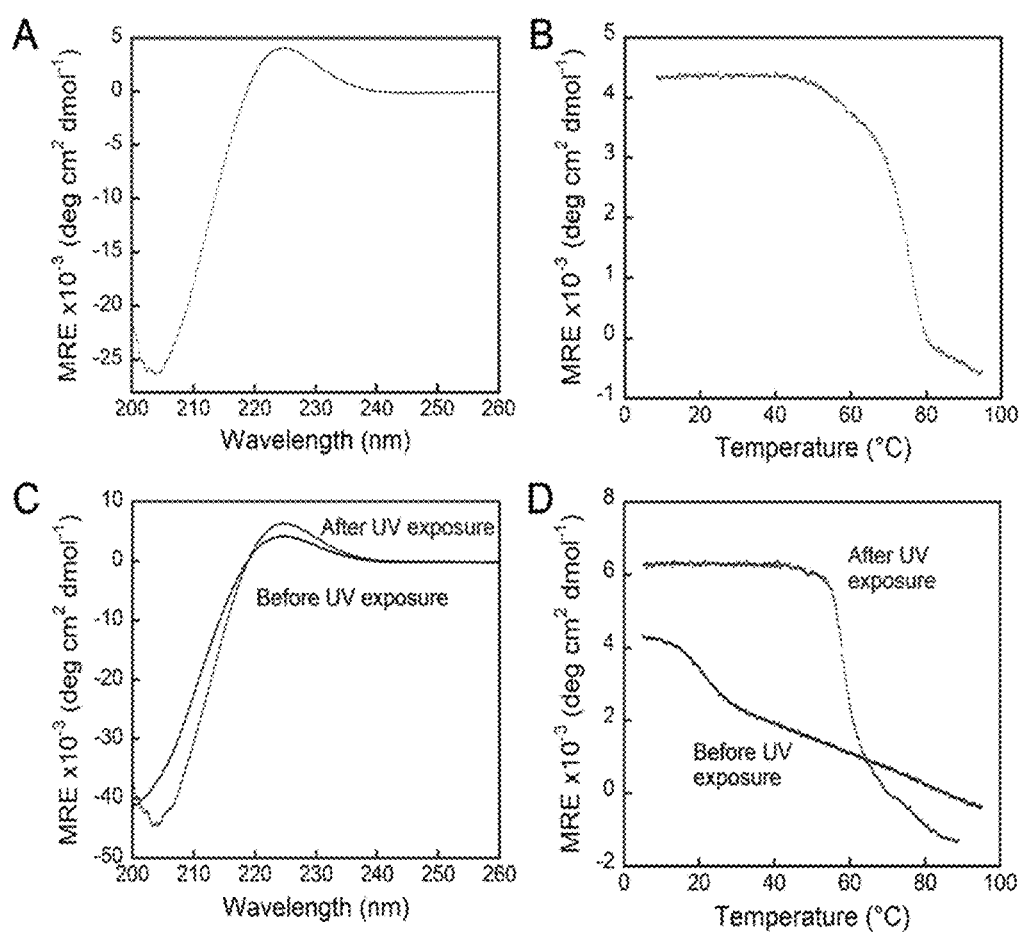
FIG. 28 shows CD studies of fluorescently labeled CMPs. (A) CD spectrum of CF(GPO)$_9$ (SEQ ID NO: 10) measured at 4° C. (B) CD melting curve of CF(GPO)$_9$ (SEQ ID NO: 10) with a melting temperature (T$_m$) of 75° C. The CD spetra (C) and melting curves (D) of TAMRA-$^{NB}$(GPO)$_9$ (SEQ ID NO: 12) before and after UV exposure. The CD study demonstrates that the CMP regains its triple helical folding capacity after photo-cleavage of the NB cage group, similar to the photo-cleavage of NB of the CF$^{NB}$(GPO)$_9$ (SEQ ID NO: 4).[2] All samples were dissolved in PBS solutions and incubated at 4° C. for at least 24 hr before CD measurement to ensure folding. All melting curves (in B, D) were generated by monitoring CD signals at 225 nm with a 1° C./min heating rate.

Synthesis of fluorescently labeled collagen mimetic peptides. Non-caged CMPs were synthesized using Fmoc-mediated solid-phase chemistry by manual or automated synthesis as described previously.2,4 The caged NB(GPO)$_9$ (SEQ ID NO: 12) was prepared by introducing Fmoc(N-o-nitrobenzyl)Gly-OH (synthesized according to Tatsu et al. 2,5) in the middle of the standard solid-phase peptide synthesis. The Hyp residue following the NBGly was conjugated using 9 molar equiv of Fmoc-Hyp(tBu)-OH, 8.8 molar equiv of PyBroP, and 20 molar equiv of DIPEA for over 24 hr to overcome the low reactivity caused by the steric hindrance of the NB cage group. The remaining sequence including the GGG spacer was completed by HBTU chemistry, followed by on-resin labeling with 6 molar equivalent of CF or TAMRA activated by 6 molar equivalent of PyAOP for over 24 hr. The full length fluorescent CMPs were cleaved from resin by treating the resin with TFA/TIS/H2O (95:2.5:2.5) for 3 hr and the cleaved peptide was purified by reverse phase HPLC on a Vydac C18 column using a linear gradient mixture of water (0.1% TFA) and acetonitrile (0.1% TFA) (5-45% acetonitrile gradient in 40 min). The purified peptides were analyzed by MALDI-TOF MS (FIG. 27): m/z calculated 2975.1 [M+Na+] for CF(GPO)$_9$ (SEQ ID NO: 10), found 2975.0 [M+Na+]; m/z calculated 2975.1 [M+Na+] for $^S$G$_9$P$_9$O$_9$ (SEQ ID NO: 5), found 2973.5 [M+Na+]; m/z calculated 3110.2 [M+Na+] for CF$^{NB}$(GPO)$_9$ (SEQ ID NO: 4), found 3109.4 [M+Na+]; m/z calculated 2975.1 [M+Na+] for CF(GPO)$_9$ (SEQ ID NO: 10) [CF$^{NB}$(GPO)$_9$ (SEQ ID NO: 4) after UV decaging], found 2974.1 [M+Na+]; m/z calculated 3142.3 [M+H+] for TAMRA-NB(GPO)$_9$ (SEQ ID NO: 12), found 3141.4 [M+H+]; m/z calculated 3007.2 [M+H+] for TAMRA-(GPO)$_9$ (SEQ ID NO: 15), [TAMRA-NB(GPO)$_9$ (SEQ ID NO: 12) after decaging], found 3006.3 [M+H+]. CD spectra and CD melting curves of the labeled CMPs were acquired in PBS solutions using a JASCO 715 CD spectrophotometer. The solutions were incubated for at least 24 hours at 4° C. prior to CD experiment to ensure folding (FIG. 28).

SDS-PAGE staining and imaging. Proteins were resolved on NuPAGE® Novex 4-12% bis-tris gels under denaturing conditions using an XCell SureLock™ Mini-Cell electrophoresis system (Life Technologies). NuPAGE® MOPS SDS running buffer containing 50 mM MOPS, 50 mM Tris Base, 0.1% SDS, and 1 mM EDTA (pH 7.7) was used. Protein samples were heated to 85° C. in NuPAGE® LDS sample denaturing buffer for 10 min before the gel loading. Unless specified otherwise, 2 μg of protein was used for each lane. The gels were run at 200 V for 50-60 min. Reducing conditions were used only for gels carrying type IV collagen, HUVECs lysate, and C1q, for which NuPAGE® reducing agent was mixed with the protein samples, and 500 μL of NuPAGE® antioxidant was added to the cathode buffer before loading. After electrophoresis, the gels were washed by deionized water briefly three times to remove the remaining SDS. No fixation of the protein bands was performed, except for Scl2.28CL which was found to diffuse out of the gel easily without fixation; the gel carrying Scl2.28CL (shown in FIG. 26B) was fixed using 5% (wt) glutaraldehyde for 30 min and washed with deionized water before staining. PBS solutions (3-6 mL) containing 6 μM of CF(GPO)$_9$ (SEQ ID NO: 10) (or CF$^S$G$_9$P$_9$O$_9$ (SEQ ID NO: 5)) were heated to 85° C. for 10 min and immediately pipetted onto the gels. The gels were soaked in this CMP solutions in dark under gentle shaking for 3 hr at room temperature, followed by washing with deionized water three times (1 hr each time) or overnight. The gels were then scanned using a Typhoon™ 9410 variable mode imager (Amersham Biosciences) under the settings of 488 nm blue laser excitation, 520 nm band-pass filter, 450 V of PMT, and 50 μm resolution. The dilution series of collagen I (FIG. 25A) was imaged using 600 V of PMT to examine the sensitivity limit of CF(GPO)$_9$ (SEQ ID NO: 10). The fluorescence intensities of the protein bands were quantified using GE ImageQuant™ TL software. After fluorescence imaging, all gels were further stained with coomassie brilliant blue (CB) G-250 (Bio-Rad) for 2-3 hr followed by washing, and imaging under white light illumination using a Gel Doc EQ system (BioRad).

Immunohistochemistry. Frozen fixed tissue slides were allowed to equilibrate to room temperature and dried under air flow. The tissue sections were permeabilized by cold methanol at −20° C. for 10 min, and incubated in 1×PBS solution. The paraffin embedded bone sections were de-paraffinized by two cycles of 5 min xylene wash, two cycles of 5 min 100% ethanol wash, and two cycles of 5 min 95% ethanol wash followed by soaking in 1×PBS solutions. Subsequently, to each slide, 0.5 mL of blocking solution (10% v/v goat serum and 0.3% Triton X-100 in 1×PBS) was added, and allowed to react for 30 min at room temperature. CF$^{NB}$(GPO)$_9$ (SEQ ID NO: 4), CF$^S$G$_9$P$_9$O$_9$ (SEQ ID NO: 5) or TAMRA-$^{NB}$(GPO)$_9$ (SEQ ID NO: 12) were dissolved in 1×PBS solution containing anti-collagen I antibody (1:100 dilution), 0.1% BSA and 0.3% Triton X-100. After blocking, CMP solutions of designated concentrations were applied to the tissue sections (100 μL for each slide) and allowed to incubate for 10 min. The CMP folding and collagen binding were triggered by exposing the samples to UV light (~15 mW/cm$^2$) for 5-12 min (incubation time depends on CMP concentration). After irradiation, the tissue sections were gently covered by parafilms to prevent drying and incubated in a humidity chamber at 4° C. for over 1.5 hr. The tissue slides were then washed by soaking in 1×PBS solutions for 5 min three times and probed by Alexa Fluor® 594 F(ab')$_2$ fragment of goat anti-rabbit IgG (1:300) for 1 hr at room temperature to visualize the anti-collagen I antibody. When necessary, DAPI solutions (1 μg/mL) were applied to the slides for 60 s before the slides were washed by PBS again. The tissue slides were dried, mounted by Prolong® Gold antifade reagent and covered with glass cover slips. The stained sections were imaged by a Nikon Eclipse TE2000-E microscope (Nikon Instruments, Melville, N.Y.) Ammonium acetate solutions (50 mM) containing 1 mM of $CuSO_4$ were applied directly to the tissue sections to reduce the background autofluorescence during imaging liver tissues.

Example 1

Design and photo-triggered folding of the caged collagen mimetic peptide.

Figure 5:
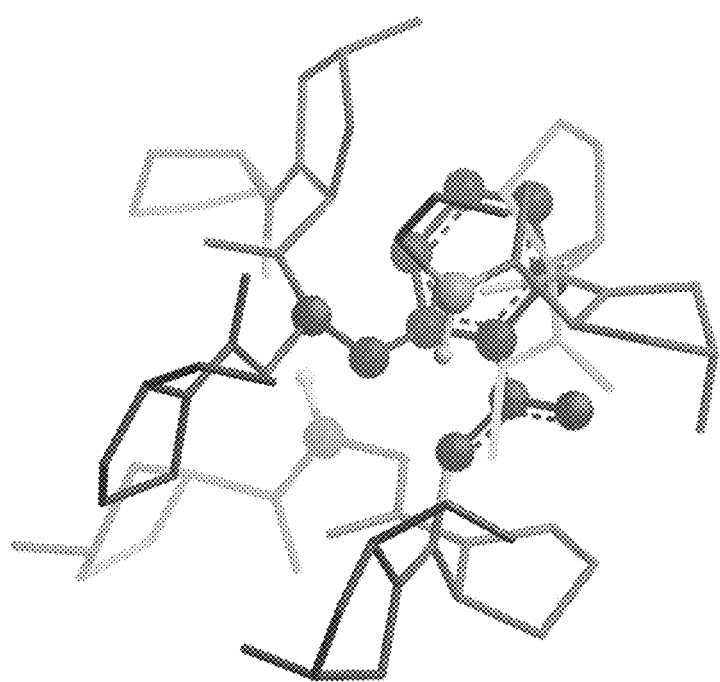
FIG. 5 is a computer-generated image (viewed in the direction of the helical axis) of a hypothetical CMP [(Gly-ProHyp)$_x$] triple helix. Single NB-cage substitution on Gly nitrogen on one CMP strand is shown in purple ball-and-stick model, highlighting the steric clashes with the neighboring chains.

In the collagen triple helix, small Gly residues are periodically located at every third position in each collagen strand to allow close packing of three protein chains in a right-handed twist (FIG. 1A). Mutations at even a single Gly position can destabilize the collagen structure and cause debilitating genetic disease. A large, sterically hindered, photo-cleavable cage group was conjugated to the central Gly nitrogen of the CMP in order to fully negate the CMP's ability to fold (FIG. 5), while exposure to light could liberate the cage group, and trigger triple helix folding and collagen binding. The nitrobenzyl (NB) caged and carboxyfluorescein (CF) labeled CMP of sequence CF-Gly$_3$-(GlyPro-Hyp)$_4$-$^{NB}$GlyProHyp-(GlyProHyp)$_4$ (SEQ ID NO: 4) [designated as $CF^{NB}(GPO)_9$ (SEQ ID NO: 4), FIG. 1B] was synthesized by incorporation of Fmoc(N-o-nitrobenzyl)Gly-OH during conventional Fmoc-mediated solid phase peptide synthesis (SPPS). Coupling of Hyp to the sterically hindered $^{NB}$Gly termini of the growing peptide was sluggish under HBTU/HOBT coupling condition; however with the more powerful activating agent, PyBroP (*Org Lett* 9:2249-2252 (2007)), we were able to achieve almost quantitative coupling efficiency and continue coupling the remaining peptide by SPPS, including the triple Gly spacer and the CF fluorescent tag (FIG. 6).

Figure 7:
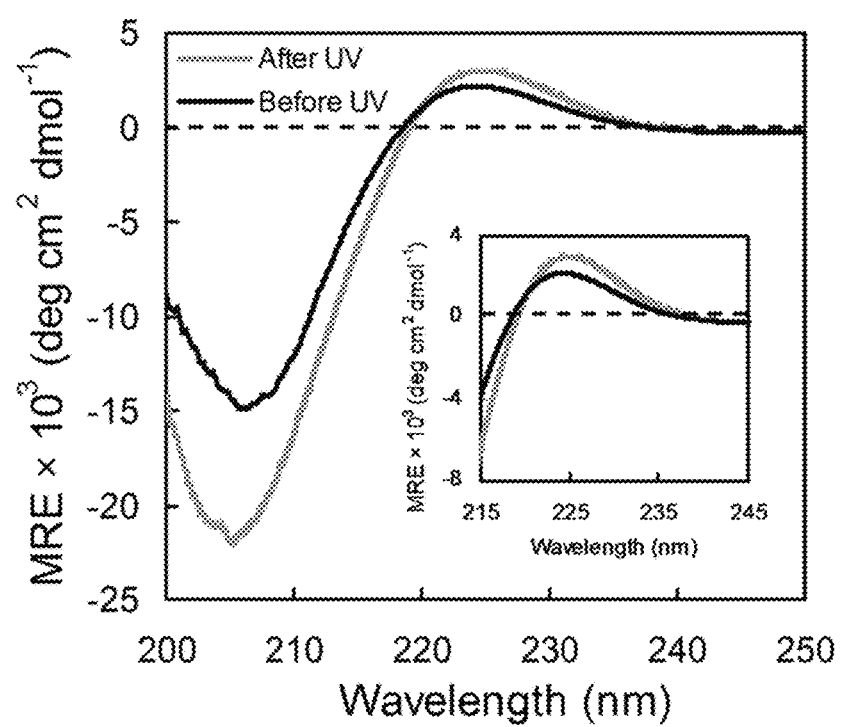
FIG. 7 shows CD spectra of CF$^{NB}$(GPO)$_9$ (SEQ ID NO: 4) solutions (150 μM in 1×PBS) at 4° C. before and after UV exposure. Both samples were incubated at 4° C. for at least 24 hours before CD measurement to ensure folding. The CD spectrum of CF$^{NB}$(GPO)$_9$ (SEQ ID NO: 4) before UV exposure at 4° C. showed a reduced positive peak near 225 nm (highlighted in inset) and a negative peak at 205 nm, suggesting a polyproline II helix conformation.

As anticipated, $CF^{NB}(GPO)_9$ (SEQ ID NO: 4) exhibited photo-triggered triple helix folding behavior (FIG. 1C-E). The NB cage group completely suppressed the CMP's ability to fold into a triple helix as evidenced by the linear CD intensity decrease during melting (FIGS. 1D, 7). Exposure to UV light (365 nm, ~10 mW/cm$^2$) efficiently cleaved the NB (FIG. 1C, Table 1) which allowed the CMP to regain its full triple helical folding capacity as exhibited by the sigmoidal CD melting curve (heating rate: 60° C./hr) with $T_m$ at 75° C. and fast refolding kinetics after thermal quenching from 80° C. to 25° C. (FIGS. 1D, E).

Example 2

Photo-triggered CMP-collagen hybridization.

Figure 2:
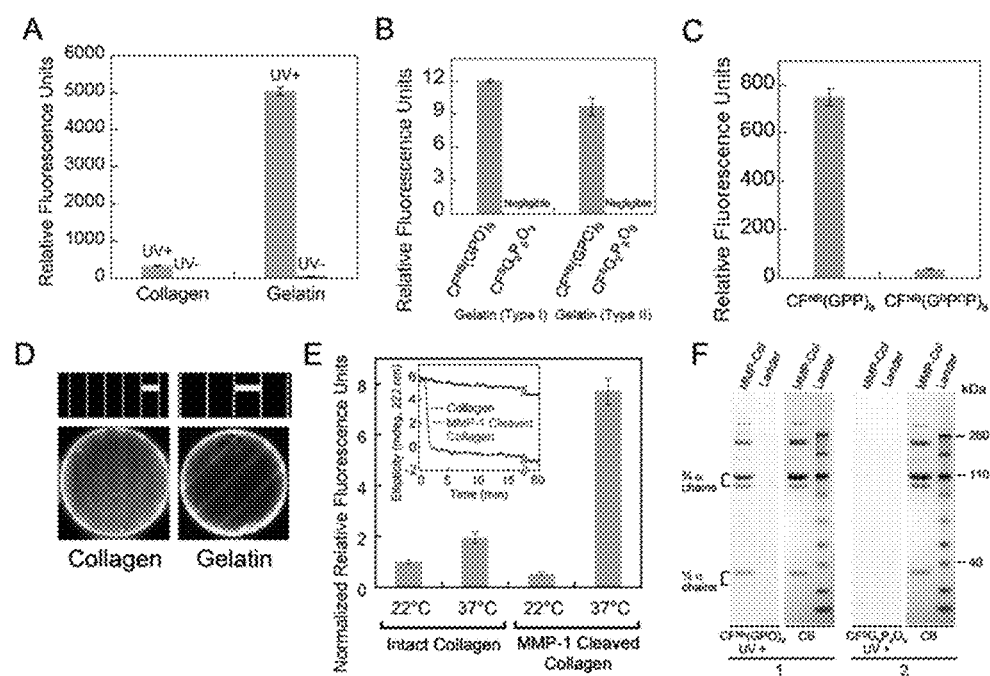
FIG. 2 depicts the characterization of photo-triggered CMP-collagen hybridization. (A) Fluorescence levels of collagen films (fibrillar collagen) and thermally-denatured collagen (gelatin) films treated by $CF^{NB}(GPO)_9$ (SEQ ID NO: 4) with and without UV exposure. (B) Comparative fluorescence levels of type I and type II gelatin coatings treated with UV-exposed $CF^{NB}(GPO)_9$ (SEQ ID NO: 4) and the sequence-scrambled control peptide, $^SG_9P_9O_9$ (SEQ ID NO: 5) (CF-GGG-PGOGPGPOPOGOGOPPGOOPG-GOOPPG (SEQ ID NO: 5)). (C) Fluorescence levels of type I gelatin films treated with UV-exposed CFNB(GPP)9 (SEQ ID NO: 6) and control peptide of opposite helicity, $CF^{NB}(G^DP^DP)9$. (D) Fluorescence photographs of the photo-patterned collagen (left) and gelatin (right) films along with photographs of the transparency masks (top, in scale with the photo-patterned films below) showing the line patterns [scale bars: 2 mm (left), 3 mm (right)]. (E) Comparative fluorescence levels after photo-triggered $CF^{NB}(GPO)9$ (SEQ ID NO: 4) binding to non-fibrillar form of intact or MMP-1 cleaved type I collagens before and after 1 minute of 37° C. incubation. Inset: CD signals after a temperature jump from 22° C. to 37° C. indicated fast denaturation (90% signal reduction in less than 3 min) of MMP-1 digested type I collagens at 37° C. while intact collagen maintained most of its triple helical structure. (F) Fluorescence images of SDS-PAGE gels of MMP1-cleaved type I collagen (MMP-Col) and protein ladder stained with $CF^{NB}(GPO)9$ (SEQ ID NO: 4) (gel 1) or $^SG_9P_9O_9$ (SEQ ID NO: 5) (gel 2) upon UV-activation, and white light photographs of the same gels stained with coomassie brilliant blue (CB). Bands labeled as ¾α and ¼α chains are MMP-1 digested collagen fragments. All CMP binding assays were performed in triplicate (±s.d.).
Figure 8:
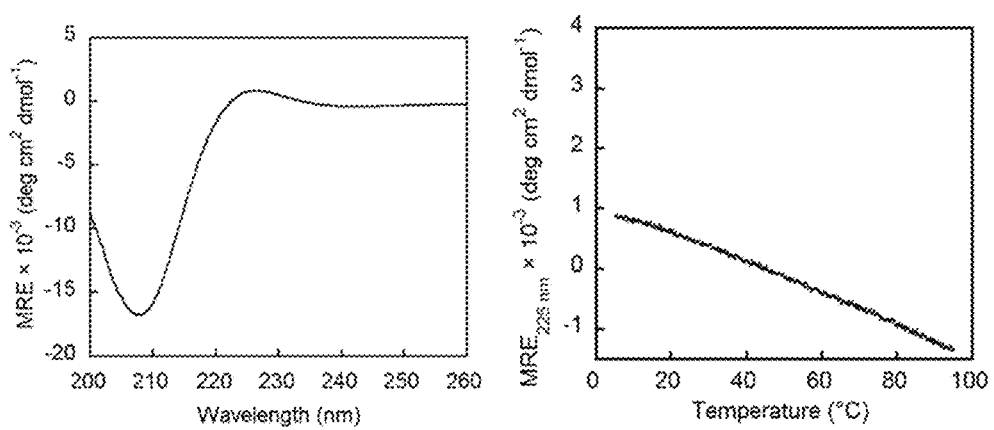
FIG. 8 is a CD spectrum (left) and melting curve (right) of $^S$G9P9O9 (SEQ ID NO: 5) solutions (150 μM in 1×PBS). The low peak ellipticity value at 225 nm and the linear ellipticity decrease during thermal melting indicate lack of triple helical structure. Samples were incubated at 4° C. for at least 24 hours before CD measurement to ensure folding.

Using the new caged CMP, a comparative study of CMP binding towards intact and thermally denatured (gelatin) type I collagen was performed because collagen denaturation could be completely decoupled from CMP melting. Photo-triggered binding affinity of the caged CMP was studied by applying $CF^{NB}(GPO)_9$ (SEQ ID NO: 4) to a 96-well assay microplate coated with collagen/gelatin films, followed by UV (365 nm) exposure and measuring the fluorescence intensity of the collagen films after washing. While caged CMP binding (UV−) remained negligible on both collagen and gelatin substrates, photo-activated caged CMPs (UV+) exhibited binding to both substrates with the level of binding an order of magnitude higher for gelatin (FIG. 2A). These results indicate that CMP's triple helical folding is required for the binding, and collagen denaturation produces unfolded collagen strands that avidly hybridize with photo-decaged CMPs. The binding affinity was further confirmed for both type I and type II gelatin in comparison to sequence-scrambled CMPs which exhibited no triple helical folding capacity (FIG. 8) and negligible affinity to gelatin (FIG. 2B).

Figure 9:
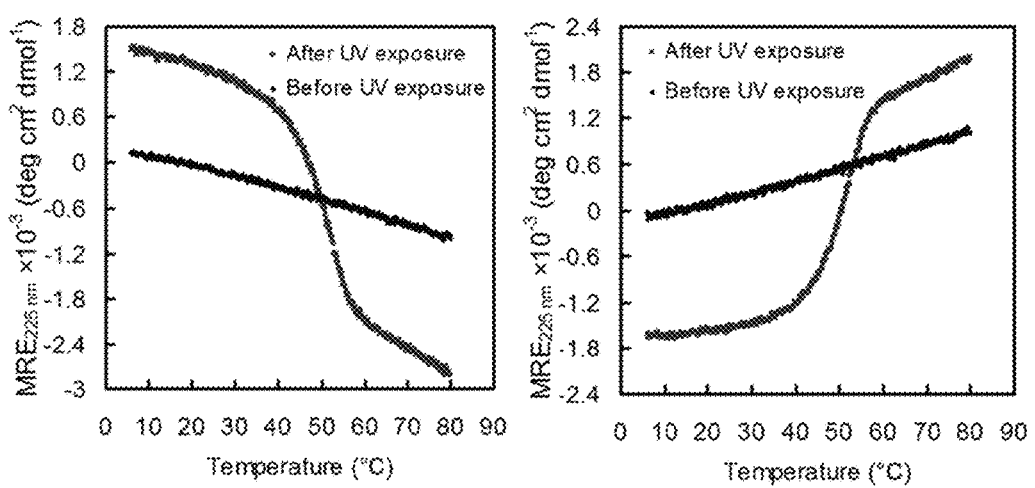
FIG. 9 shows CD melting curves of CFNB(GPP)$_9$ (SEQ ID NO: 6) (left) and CF$^{NB}$(G$^D$P$^D$P)$_9$ (right) before and after UV exposure. Both peptides transformed from single stranded state to folded state after UV exposure, forming triple helices of identical Tm at 51° C., but of opposite helical twist as evidenced by the mean residue ellipticity values of opposite signs. All samples were incubated at 4° C. for at least 24 hours before CD measurement to ensure folding.

Although these experiments demonstrated collagen binding mediated by CMP's ability to fold into a triple helix, questions remain as to the precise mechanism underlying the CMP-collagen interactions. This question was addressed by studying the collagen affinity of a specially synthesized CMP composed of D-proline ($^D$P) which folds into an oppositely twisted left-handed triple helix. Since D-hydroxyproline is not readily available, two caged Hyp-free CMPs were synthesized; $CF^{NB}(GPP)_9$ (SEQ ID NO: 6), which folds into a natural right handed twist, and $CF^{NB}(G^DP^DP)_9$, which was expected to fold into an unnatural left handed twist after photo-decaging. The CD melting curves of the two peptides after photo-cleavage were exact mirror images with identical $T_m$ at 51° C. (FIG. 9). Despite almost identical CD melting behaviors, $CF^{NB}(G^DP^DP)_9$ exhibited an order of magnitude lower levels of gelatin binding to that of $CF^{NB}(GPP)_9$ (SEQ ID NO: 6) after photo-cleavage (FIG. 2C). Natural collagen strands can only fold into right handed triple helices and are unlikely to form a triple helical hybrid with a CMP having propensity for a left handed twist. The results clearly show that the binding is not due to CMP trimers merely trapping the gelatin strands during triple helical assembly, but that it is primarily driven by stereo-selective CMP-collagen strand hybridization, most likely in the form of a triple helix.

Figure 10:
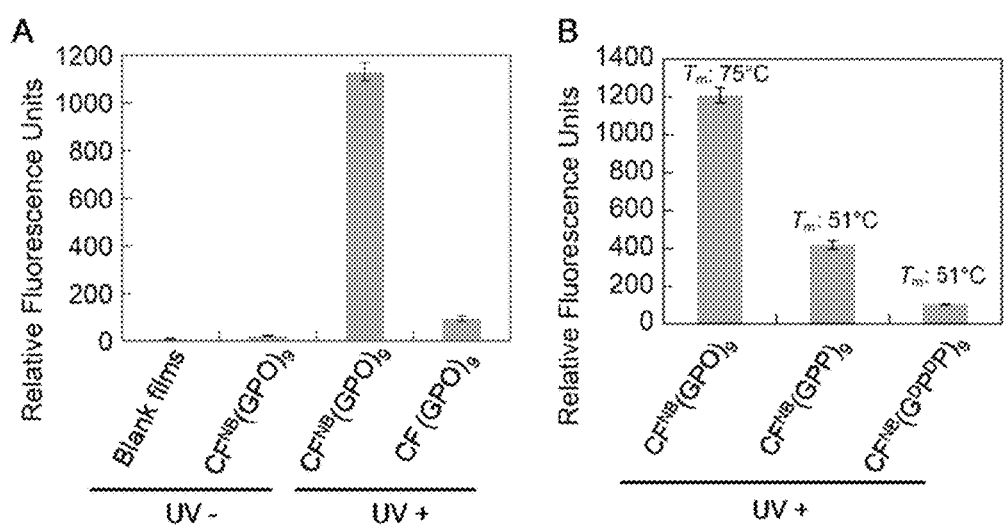
FIG. 10 depicts photo-triggered CMP binding to intact type I collagens. (A) Fluorescence levels of type I collagen films (fibrillar collagen) treated with CF$^{NB}$(GPO)$_9$ (SEQ ID NO: 4) (40 μL/well, 100 μM in 1×PBS, with and without UV exposure) and triple helical CF(GPO)$_9$ (SEQ ID NO: 10) (40 μL/well, 100 μM in 1×PBS, pre-equilibrated at 4° C., with UV exposure). (B) Fluorescence levels of type I collagen films (fibrillar collagen) treated with CMP derivatives after UV-induced binding. CF$^{NB}$(GPO)$_9$ (SEQ ID NO: 4) , CFNB (GPP)$_9$ (SEQ ID NO: 6) and CF$^{NB}$(G$^D$P$^D$P)$_9$ (40 μL/well, 100 μM in 1×PBS) were decaged by UV irradiation directly on collagen films. The CMPs were incubated on collagen films overnight to ensure folding due to the low folding rate of the Hyp-free CMPs. The low collagen binding of CF(GD-PDP)$_9$ compared to CF(GPP)$_9$ (SEQ ID NO: 11) despite nearly identical CD melting behavior suggests that CMP-collagen binding involves multiplex hybridization (most likely in a triple helix form) that is sensitive to the stereochemistry of individual strands. All CMP binding assays were performed at 4° C. in triplicate (±s.d.).
Figure 11:
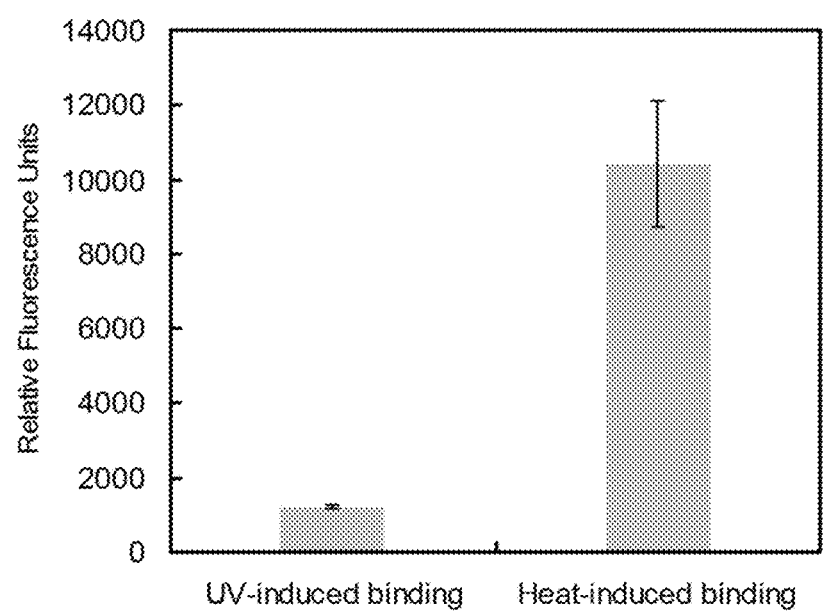
FIG. 11 is a graph of Fluorescence levels of CF(GPO)$_9$ (SEQ ID NO: 10) immobilized on collagen films (fibrillar collagen) by UV- or heat-induced binding. To trigger binding, non-caged CF(GPO)$_9$ (SEQ ID NO: 10) (40 μL/well, 100 μM in 1×PBS) was first melted at 75° C. for 10 min and applied to collagen films (heat-induced), while the same amount of CF$^{NB}$(GPO)$_9$ (SEQ ID NO: 4) was exposed to UV light for 22 min on top of collagen films at room temperature (UV-induced). Both collagen films were then incubated for 3 hr at 4° C. to ensure CMP binding. Adding heated non-caged CF(GPO)$_9$ (SEQ ID NO: 10) directly to collagen films resulted in significantly higher binding level than the photo-triggered binding due to the heat-induced denaturation of the collagen substrates. The binding assays were performed in triplicate (±s.d.).

To investigate the low but apparent CMP binding affinity to intact collagen film (FIG. 2A), a series of binding experiments was performed using a non-caged, triple helical $CF(GPO)_9$ (SEQ ID NO: 10) and UV-triggered $CF^{NB}(GPP)_9$ (SEQ ID NO: 6)/$CF^{NB}(G^DP^DP)_9$ pair, as well as thermally melted single-stranded $CF(GPO)_9$ (SEQ ID NO: 10) (FIGS. 10, 11). The results confirm that CMP's binding affinity to intact type I collagen is real and also stereo-selective. The density of photo-induced CMP binding to intact collagen was determined to be as high as 0.56±0.03 nmol/cm$^2$, which is well above the bioactive ligand density for a variety of cell scaffold interactions in cell culture and tissue development. Using $CF^{NB}(GPO)_9$ (SEQ ID NO: 4), photo-pattern collagen and gelatin films was also performed, and which demonstrated the potential for local immobilization of CMP conjugated bioactive components to collagen-containing tissue engineering scaffolds (FIG. 2D).

Since many pathologic conditions are associated with collagen remodeling by MMP activity, degraded collagens in diseased tissue and circulation are potential diagnostic and therapeutic targets. Anti-collagen antibodies and low molecular weight targeting agents have been used to image collagens in fibrotic tissues and tumors, but they suffer from poor pharmacokinetics, and/or low specificity and binding affinity. The caged CMP [$CF^{NB}(GPO)_9$ (SEQ ID NO: 4)]'s photo-triggered binding affinity to type I collagen after MMP-1 digestion was tested (FIG. S8 for SDS-PAGE and CD characterization). MMP-1 cleaves the ¾ position of the collagen molecule resulting in two collagen fragments with $T_m$ around 34° C. that spontaneously denature at body temperature (FIG. 2E, inset). The photo-triggered CMP binding assay was performed on intact and MMP-1 digested collagens before and after incubation at 37° C. For intact collagens, the level of CMP binding was similarly low for the two temperature conditions. In contrast, MMP-1 digested collagens after the 37° C. incubation exhibited approximately 4-10 fold higher levels of CMP binding compared to all other collagens tested (FIG. 2E). These results show that CMPs preferentially hybridize with MMP-1 digested collagens, which are spontaneously denatured at body temperature, over intact collagens. This hybridization was further verified by a SDS-PAGE staining experiment. When used as a gel staining agent, only the photo-cleaved CMP, and not the scrambled control peptide, was able to stain the MMP-1 digested collagen bands (FIG. 2F). No other bands from the protein ladder were stained by the CMP which demonstrates its high binding specificity to collagen chains.

Example 3

In vivo tumor targeting by CMP hybridization.

Figure 3:
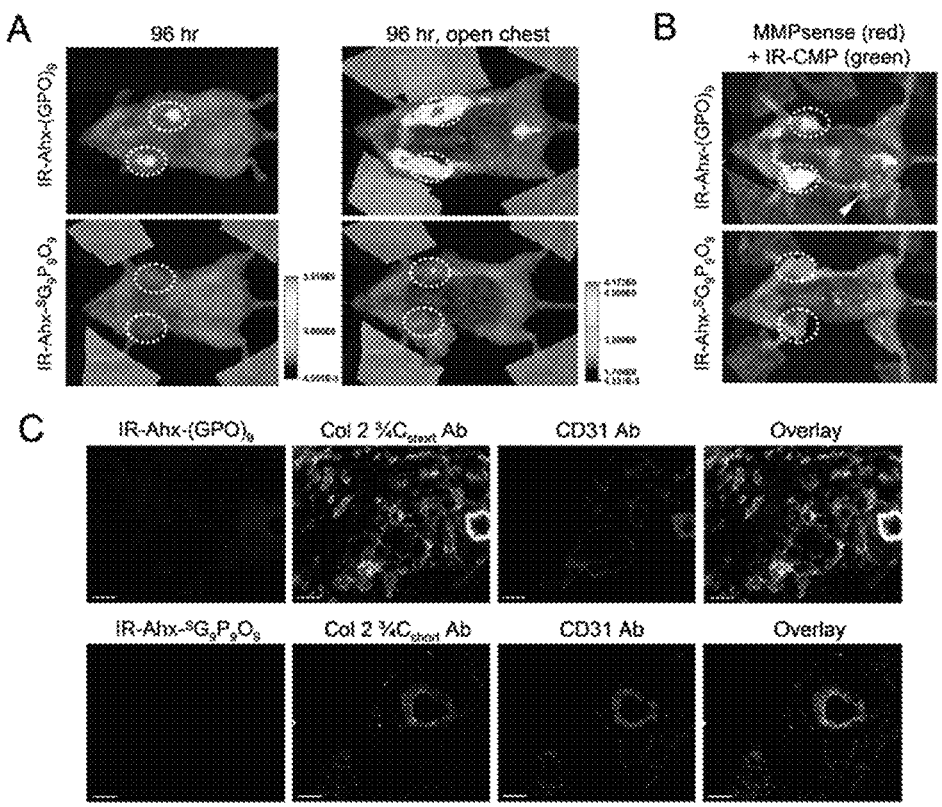
FIG. 3 shows in vivo targeting of tumors by CMP hybridization with MMP-digested collagens. (A) In vivo NIRF images of mice bearing PC-3 prostate tumors at forward right and left flanks (circled) administered with 3.7 nmol of UV-activated $IR-Ahx-^{NB}(GPO)_9$ (SEQ ID NO: 7) or sequence-scrambled control peptide, $IR-Ahx-^SG_9P_9O_9$ (SEQ ID NO: 8) via tail vein injection. Ventral views of both mice at 96 hours post-injection (PI), and after midline surgical laparatomy (open chest) indicate tumor specific and stable accumulation of only the $IR-Ahx-(GPO)_9$ (SEQ ID NO: 9) and not the control peptide. (B) NIRF images of another pair of mice bearing PC-3 tumors at the same location at 102 hours after IR-CMP injection and 24 hours after MMPSense680 injection, showing co-localization (in yellow) of MMP activity (red) and CMP binding (green) in the tumors (circled) and knee joint (arrowhead).
Figure 14:
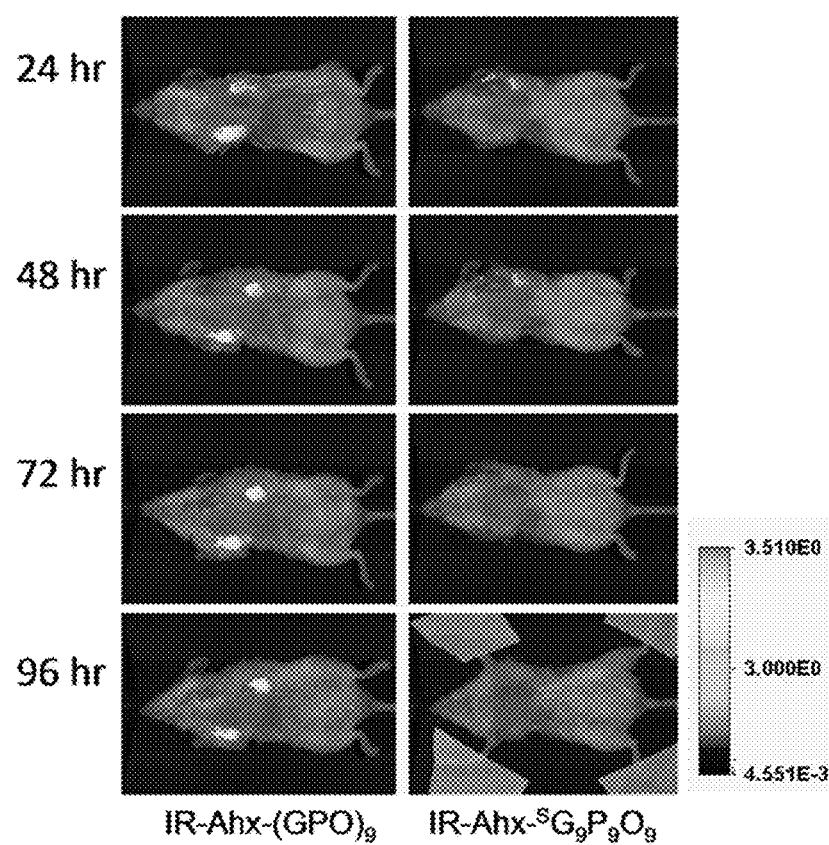
FIG. 14 shows In vivo fluorescence images of NOD/SCID mice bearing PC3-PIP (forward right flank) and PC3-flu (forward left flank) tumors. A pair of NOD/SCID mice were dosed with either 3.7 nmol of photo-decaged IR-Ahx-NB (GPO)$_9$ (SEQ ID NO: 7) or same amount of IR-Ahx-SG9P9O9(SEQ ID NO: 8). Nair hair remover product was used on the entire ventral tumor region in both mice to remove fur and enhance optical imaging. Ventral views of both mice were obtained at 24 hours, 48 hours, 72 hours, and 96 hours post injection (PI). Photo-activated IR-Ahx-NB (GPO)$_9$ (SEQ ID NO: 7) was specifically retained by both tumors through 96 hours PI while the scrambled CMP, IR-Ahx-SG9P9O9 (SEQ ID NO: 8) was cleared out.

To demonstrate CMP's ability to target pathologic tissues of high MMP activity, an in vivo tumor targeting experiment was performed using the same caged CMP conjugated to a near-infrared fluorophore (NIRF). Tumor progression involves proteolytic remodeling of the extracellular matrix (ECM) by various MMPs that results in the accumulation of stromal collagens with a unique structural and biochemical signatures. IRDye-800CW (IR) was conjugated to the N-termini of the caged CMP $^{NB}$(GPO)$_9$ (SEQ ID NO: 17) and the scrambled peptide $^S$G$_9$P$_9$O$_9$ (SEQ ID NO: 18) with flexible aminohexanoic acid (Ahx) spacers. The NIRF labeled CMPs were rapidly decaged under intense UV light (365 nm, >25 mW/cm$^2$) and immediately injected into the tail vein of mice bearing subcutaneous PC-3 prostate tumor xenografts. Considering the slow folding rate of the CMP triple helix (half time of CMP refolding is approximately 50 minutes) and the short time delay before the injection (<5 minutes), most of the CMPs were expected to enter the blood stream in single stranded form. Once in the blood, the CMP solution is diluted by a factor of 20 which results in dramatic reduction in the folding rate because of the third order folding kinetics. Therefore, we expected that the single stranded CMPs would be able to circulate the body and eventually bind to denatured collagen strands by triple helical hybridization. Serial in vivo fluorescence imaging over four days indicated that the IR-Ahx-(GPO)$_9$ (SEQ ID NO: 9) was able to permeate the tumor vasculature and accumulate at the tumor sites, whereas the scrambled sequence (IR-Ahx-$^S$G$_9$P$_9$O$_9$ (SEQ ID NO: 8)) lacking triple helix folding capacity showed minimal accumulation at the tumor sites (FIG. 3A, FIG. 14). Furthermore, co-injection of mice with MMPSense680™, a fluorescent beacon for MMP activity, clearly showed the co-localization (in yellow) of MMP activity (in red) and CMP binding (in green) in the tumors 102 hours after CMP injection (FIG. 3B). Ex vivo fluorescence microscopy of the tumor sections indicated that IR-Ahx-(GPO)$_9$ (SEQ ID NO: 9) (in blue) was present near the CD31 positive perivascular tissue (in red) and co-localized in part with antibody for MMP-1 cleaved collagen fragments (in green) (FIG. 3C). This confirms that the tumor uptake was caused by CMP reaching the tumor via the blood vessels followed by binding to MMP digested collagens within the tumor tissue. Similar results were obtained for mice bearing pancreatic tumor xenografts (FIG. 15).

Example 4

In vivo targeting of collagen remodeling in bones and cartilages.

Figure 16:
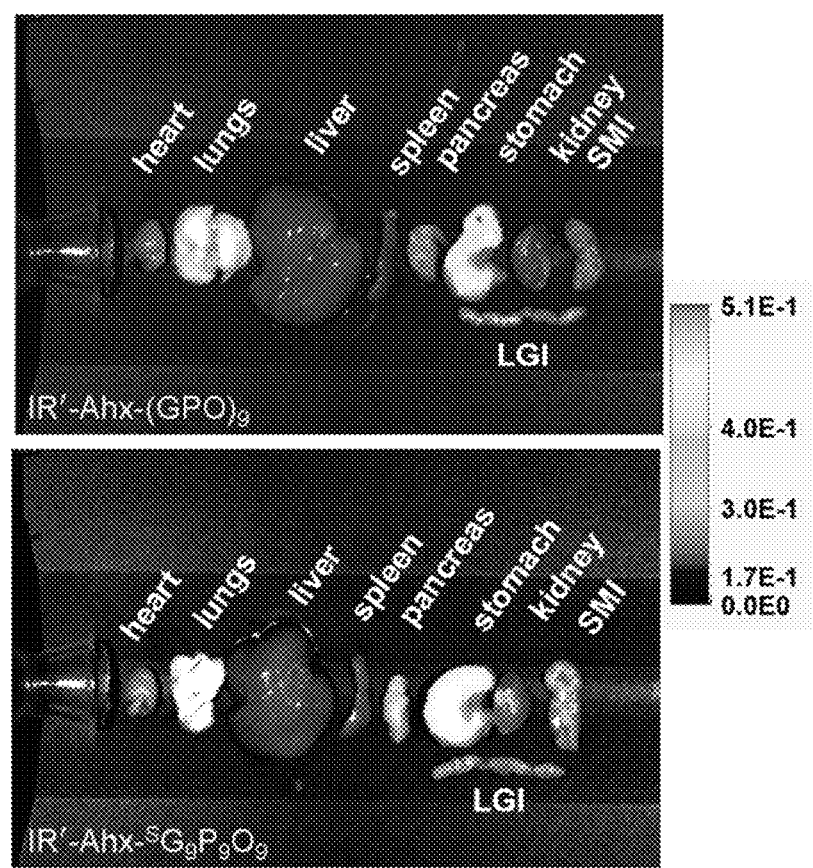
FIG. 16 depicts the organ distribution of CMPs in normal BLAB/c mice. NIRF images (96 hours post injection) of individually harvested organs from two normal BLAB/c mice each administered with 4 nmol of either photo-decaged IR'-Ahx-NB(GPO)$_9$ (SEQ ID NO: 7) or same amount of IR'-Ahx-$^S$G$_9$P$_9$O$_9$ (SEQ ID NO: 8) via tail vein injection. No apparent uptake in major organs was observed. The intensity from the stomachs and the intestines (LGI) is due to autofluorescence of the chlorophyll in food. Fluorescence intensity is shown in rainbow scale with images scaled to the same exposure time. SMI: small intestine; LGI: large intestine.

In both the prostate and pancreatic tumor targeting studies, we surprisingly observed a consistent and high level accumulation of CMPs at the knee joints, which also co-localized with MMP activity (FIG. 3B, FIG. 15A, arrowhead). Normal joints are known for continual tissue remodeling by MMP; however, targeting this area by systemic delivery is difficult due to the avascular nature of the cartilage and fast synovial fluid clearance. To study the CMP accumulation at the joints and other tissues specifically, further in vivo CMP targeting experiments were conducted using BLAB/c mice. This time, CMP conjugated to a slightly different NIRF dye, IRDye 680RD (IR') was used which has lower background fluorescence compared to 800CW. FIG. 4A shows the whole-body fluorescence image of the normal mouse four days after intravenous injection of the photo-decaged peptide. The images show clear accumulation of the CMPs within the skeleton, especially in the spine and ribs, as well as within the knees, ankles, wrists, and lower mandibles. Signals from other organs (harvested organs shown in FIG. 16) were negligible except for the digestive system, which contained fluorescent chlorophylls from food (arrows). A mouse injected with sequence-scrambled peptide (IR'-Ahx-$^S$G$_9$P$_9$O$_9$ (SEQ ID NO: 8)) showed signal only from the digestive system. Furthermore, under similar experimental condition, neither the caged-CMP lacking the folding capacity nor the pre-folded triple helical CMP showed signs of skeletal uptake after four days (FIG. 4B). These results strongly suggest that the targeting of the skeletal tissue was mainly driven by the triple helical propensity of the monomeric CMPs.

To identify the location of CMP binding more clearly, mice were co-injected with the calcium chelating fluorescent probe (IRDye800CW BoneTag™) which targets calcifying tissues. Although the overall distributions of the two probes [IR'-Ahx-(GPO)$_9$ (SEQ ID NO: 9): red; BonTag™: green] seemed similar (FIG. 4C top panel, FIG. 17A), close observation (FIG. 4C bottom panels, FIG. 17B) revealed that CMP targets both calcified and non-calcified bones (cartilages of the wrists, ribs, and knee) while the BoneTag™ targets only the calcified bones. The highest CMP intensity was detected at the articular cartilage of the knee joints (red arrow) sandwiched between two endochondral junctions (green arrows) targeted by both the BoneTag™ (green) and CMP (red). Ex vivo histologic analysis of the knee joint cartilage (unfixed frozen tissue section) showed CMP localizing at the superficial zone which was also co-stained by antibodies for MMP-1 cleaved, type II collagen fragments (FIG. 4D). The superficial zone is densely populated by type II collagen fibers, part of which are reported to be in denatured state due to steady remodeling activity. Because of continual bone remodeling, collagens within bone are metabolized throughout the lifespan, and products of collagen degradation (e.g. protein fragments, hydroxyproline) are markers for bone resorption activity. Considering the abundance of collagens in other organs, it is remarkable to see such localized and apparently stable accumulation of CMPs in the bones and joints (little reduction in fluorescence intensity over 96 hours). This suggests that the CMPs of the present invention are preferentially hybridizing with denatured collagens within the tissue and not with collagen fragments in circulation which may be too small to fold into triple helix. These results show that the CMPs of the present invention are useful as cartilage imaging agents, and appropriate derivatives can be used for bone- and cartilage-seeking therapeutics.

Figure 18:
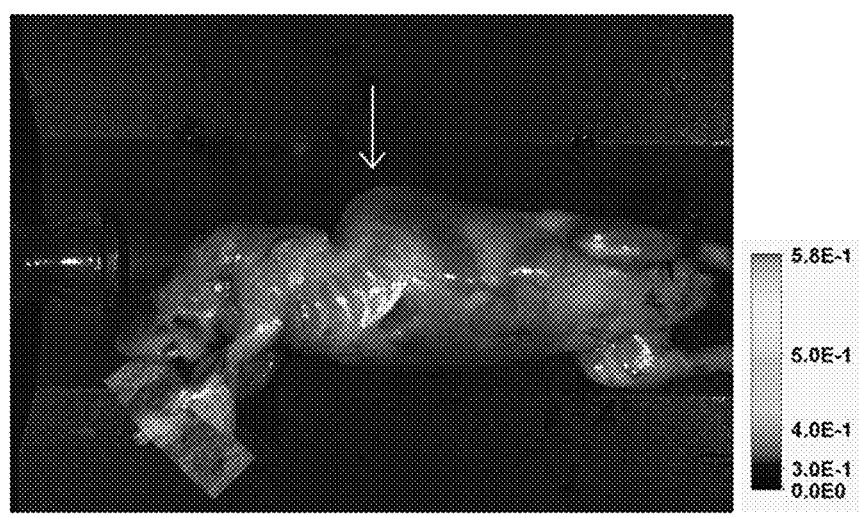
FIG. 18 shows a lateral view of a mouse model with Marfan's syndrome administrated with 4 nmol of photo-decaged IR'-Ahx-(GPO)$_9$ (SEQ ID NO: 9). The mouse was skinned and imaged 96 hours post injection. The white light image showed an apparent kyphosis (yellow arrow), while NIRF signal indicated strong uptake of IR'-Ahx-(GPO)$_9$ (SEQ ID NO: 9) in the ribs (intensity shown in rainbow scale).
Figure 20:
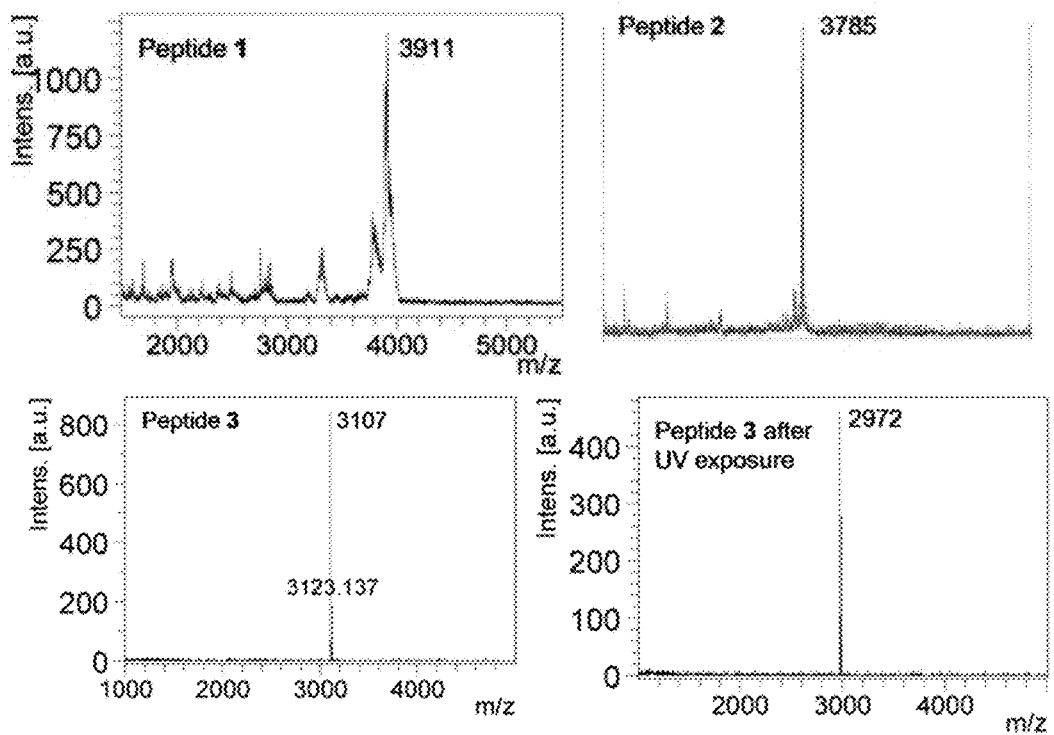
FIG. 20 shows MADLI-TOF data and spectra for CCMP peptides 1-3 of the present invention.
Figure 22:
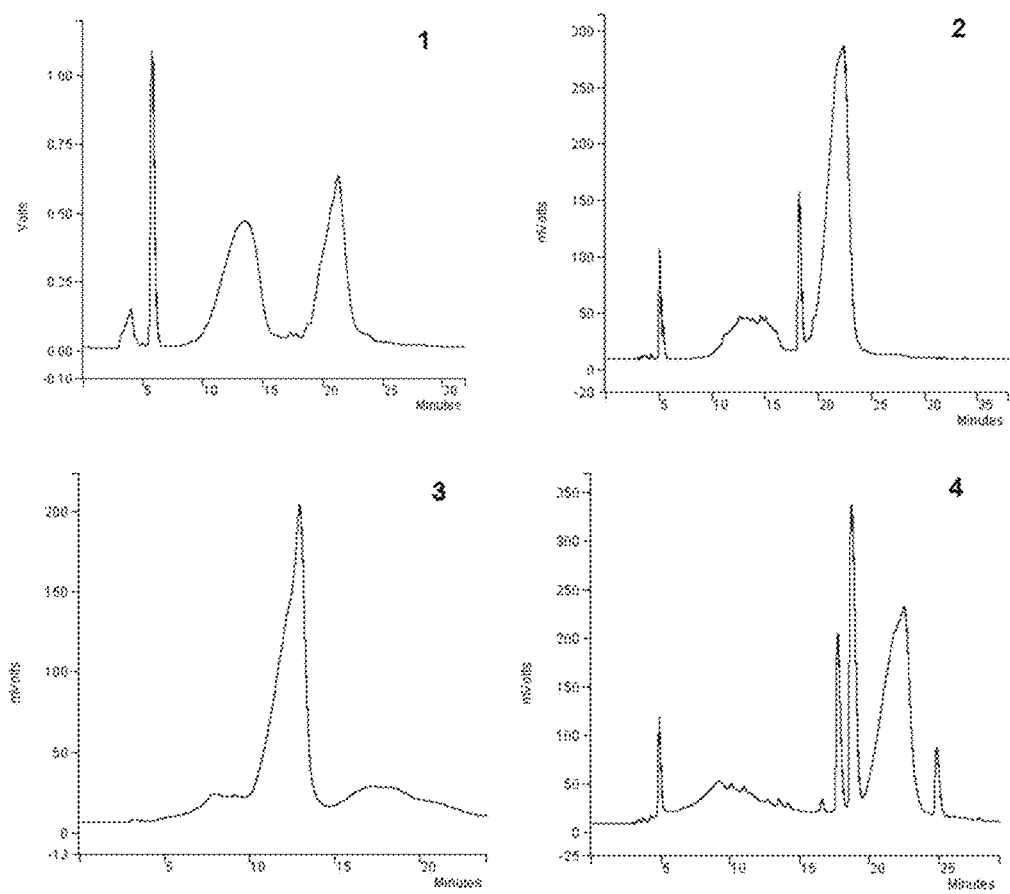
FIG. 22 shows HPLC traces for CCMP peptides 1-4.
Figure 23:
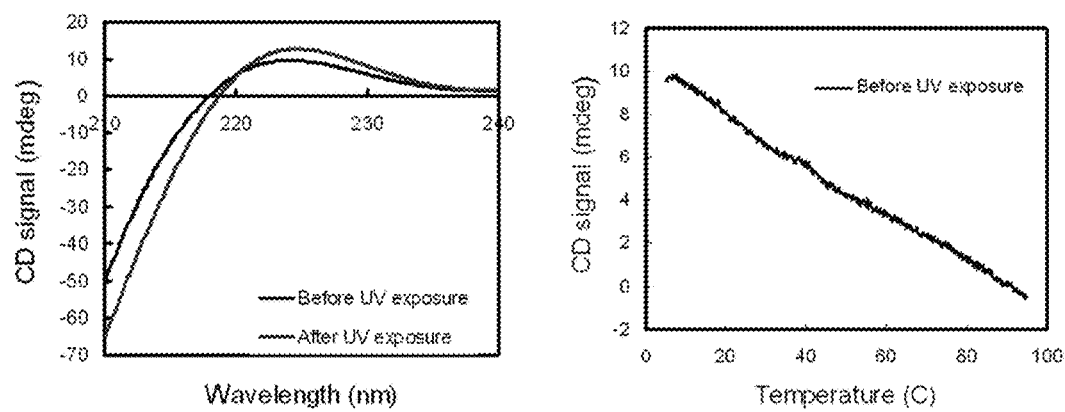
FIG. 23 shows circular dichroism (CD) spectra and melting curve of CCMP peptide 3 before and after UV exposure.

Finally, the potential for CMPs to detect bone abnormality was tested in a mouse model of Marfan syndrome, a genetic disorder of the ECM. Photo-triggered IR'-Ahx-(GPO)$_9$ (SEQ ID NO: 9) was injected into mice with a heterozygous missense mutation in fibrillin-1, which was previously shown to exhibit marked skeletal pathology, including severe kyphosis (FIG. 18) and rib overgrowth. Whole-body fluorescence images of the mutant and normal mice 96 hours after the CMP injection showed a striking difference in CMP uptake: strong CMP signal was detected at the spine and ribs of the mutant mice with at least four times the intensity of the wild-type mice (FIG. 4E). The mechanism of bone overgrowth in Marfan syndrome is complex and still not fully understood; however the strong correlation between collagen remodeling and bone growth in both physiological and pathological contexts, as well as high TGF-β signaling in multiple tissues of this mouse model support the conclusion that prominent CMP uptake in the Marfan mice, at least in part, derives from increased collagen remodeling in skeletal tissues that display pathological overgrowth.

Example 5

Photo-triggered CMP binding to the intact type I collagen.

To study the photo-triggered binding affinity of the caged CMP to intact type I collagen films, $CF^{NB}(GPO)_9$ (SEQ ID NO: 4) was applied to a 96-well assay microplate coated with reconstituted type I collagen films, and binding levels were determined with and without UV exposure by measuring the fluorescence intensity of the collagen films after washing. The entire binding assay was conducted at 4° C. to prevent thermal denaturation of the collagen films. As shown in FIG. 10A, collagen binding was observed only after exposing the sample to UV light. The photo-triggered binding of a non-caged, triple helical $CF(GPO)_9$ (SEQ ID NO: 10) was also tested. In this control experiment, CMP binding was lower by a factor of 11 compared to the UV-triggered binding of the $CF^{NB}(GPO)_9$ (SEQ ID NO: 4) (FIG. 10A, last bar). The results confirmed that CMP binding to intact collagen films is real and the triple helical folding capacity is crucial for the binding.

Similar to the gelatin binding results, CMP with left handed twist $CF^{NB}(G^DP^DP)_9$ exhibited lower levels of UV triggered collagen binding at 4° C., only about one fourth of that of $CF^{NB}(GPP)_9$ (SEQ ID NO: 6) (FIG. 10B, last two bars), confirming that the binding is not simply due to non-specific physical trapping, but it is primarily driven by stereo-selective CMP-collagen hybridization, most likely in the form of a triple helix.

Finally, heat- and UV-induced CMP binding to collagen films was compared directly. As seen in FIG. 11, thermally melted non-caged $CF(GPO)_9$ (SEQ ID NO: 10) showed significantly elevated binding levels compared to photo-triggered caged $CF^{NB}(GPO)_9$ (SEQ ID NO: 4), suggesting that in our earlier work, heat facilitated the hybridization process by partially denaturing the collagen in situ.

Example 6

In vitro collagen staining. The present inventors discovered that such strategies needed for in vivo use are not necessary for in vitro collagen staining application, since the concentration of CMP staining solutions can be very dilute (5-10 μM) with the trimerization half time in the order of hours at room temperature. Therefore it was decided to test staining of SDS-PAGE and tissue sections using dilute solutions of CMPs.

Figure 24:
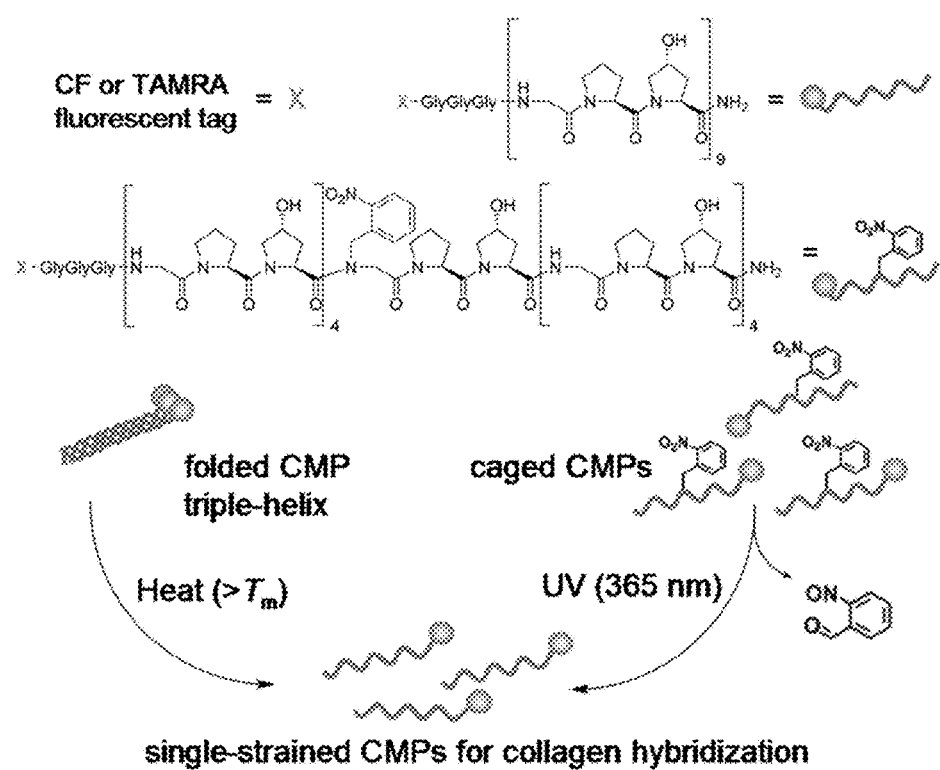
FIG. 24 shows structures of fluorescently labeled CMP and nitrobenzyl (NB) caged CMP, designated respectively as CF(GPO)$_9$ (SEQ ID NO: 10) and CF$^{NB}$(GPO)$_9$ (SEQ ID NO: 4) for CF labeled peptides, and schematic illustration of the two approaches (heat or UV activation) of generating single-stranded CMPs that can hybridize with collagen strands.

A peptide was synthesized with $(GPO)_9$ (SEQ ID NO: 15) sequence conjugated to a fluorophore through a flexible GGG linker to minimize fluorophore's influence on the peptide's triple helical folding process (FIG. 24). We chose 5(6)-carboxyfluorescein (CF) and 5(6)-carboxytetramethyl-rhodamine (TAMRA) as the fluorophores since they are compatible with standard fluorescence microscopes and imaging systems. All peptides were prepared by conventional solid-phase peptide synthesis (SPPS) using Fmoc/HBTU chemistry. The caged CMP was synthesized by inserting Fmoc(N-o-nitrobenzyl)Gly-OH in the middle of standard SPPS; the coupling reaction following the NBGly was run using excess amount of Hyp and PyBroP as previously reported. The fluorophores were conjugated to the amino termini of the peptide on the solid phase in the presence of PyAOP and DIPEA (FIG. 27). The CD spectra and thermal melting curves of the fluorescent peptides (FIG. 28) confirmed that the triple helical folding propensity of the peptides remains largely unchanged even when they are conjugated to the fluorophores. A sequence-scrambled peptide, $^CG_9P_9O_9$ (SEQ ID NO: 5) (CF-GGG-PGOGPG-POPOGOGOPPGOOPGGOOPPG (SEQ ID NO: 5)) that cannot fold into triple helix was also prepared for comparison.

Figure 25:
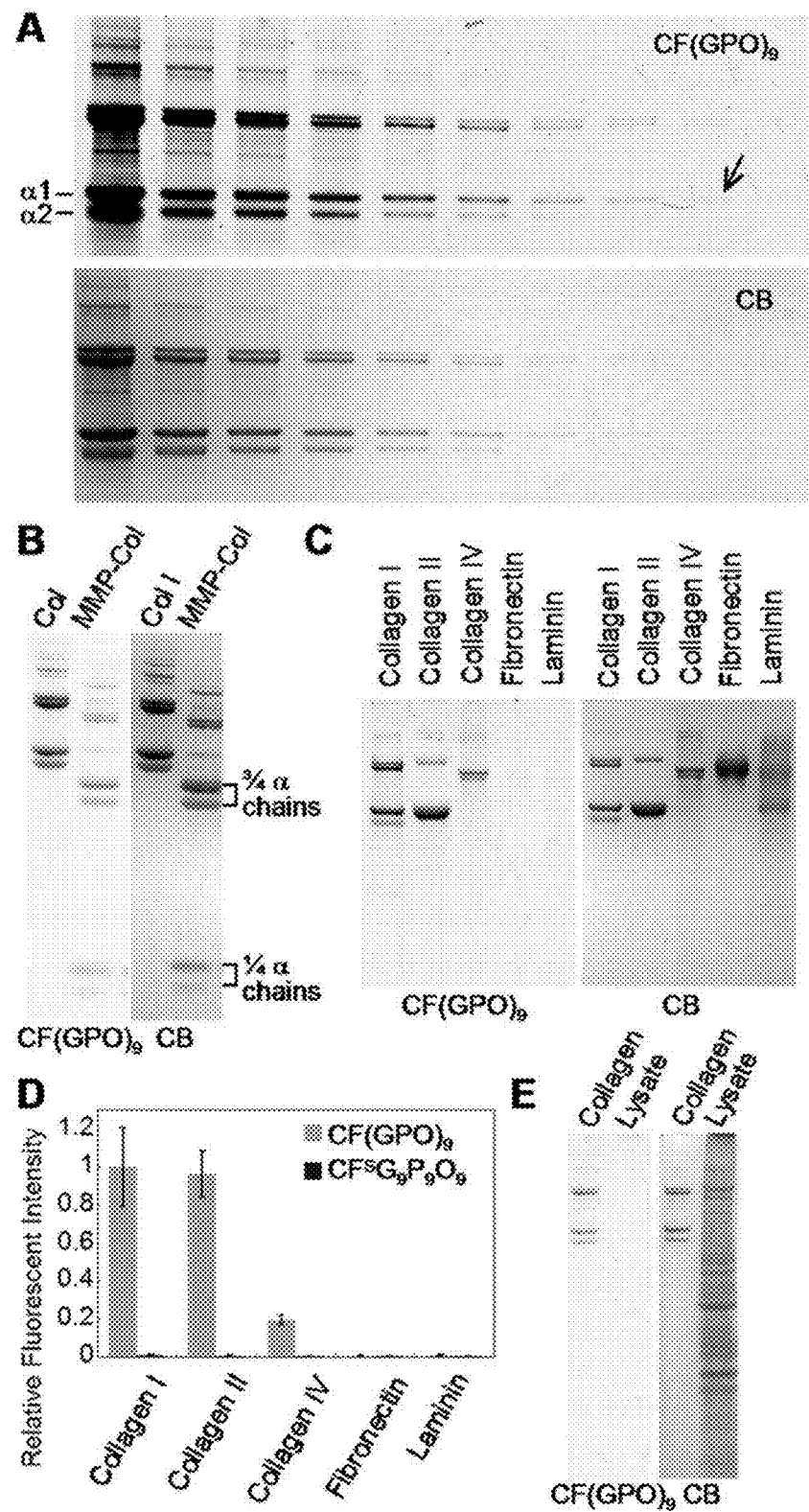
FIG. 25 depicts detection of collagen in SDS-PAGE by heat activated fluorescent CMPs. (A) SDS-PAGE loaded with a dilution series of type I collagen, stained and imaged first with CF(GPO)$_9$ (SEQ ID NO: 10) (top panel) followed by coomassie blue (CB) staining (bottom panel). From left to right, each lane was loaded with 4 μg, 2 μg, 1 μg, 500 ng, 250 ng, 125 ng, 62.5 ng, 31.2 ng, 15.6 ng and 7.8 ng of denatured collagen, respectively. The arrow points to the least recognizable band in the image which contains approximately 5 ng of collagen α1 chains. (B) SDS-PAGE of intact and MMP-1 cleaved type I collagens (3 μg in each lane) similarly stained with CF(GPO)$_9$ (SEQ ID NO: 10) and CB. (C) SDS-PAGE loaded with collagen type I, II, IV, fibronectin and laminin (2 μg of each protein), and stained with CF(GPO)$_9$ (SEQ ID NO: 10) and CB. (D) Comparative fluorescence levels of the ECM protein bands in SDS-PAGE stained by CF(GPO)$_9$ (SEQ ID NO: 10) (C) or CF$^S$G$_9$P$_9$O$_9$ (SEQ ID NO: 5) (FIG. 29). The measured fluorescence intensities were normalized by collagen I, and the experiment was performed in triplicate (±s.d.). (E) SDS-PAGE of collagen I (0.7 μg) and a lysate of HUVECs stained by CF(GPO)$_9$ (SEQ ID NO: 10) and CB showing remarkable specificity of CMP for collagen detection. Images of the CF(GPO)$_9$ (SEQ ID NO: 10) stained gels were recorded using a Typhoon fluorescent imager ($\lambda_{ex}$=488 nm), and CB stained gels were photographed using a Gel Doc EQ system.

To test the CMP's collagen probing capacity in SDS-PAGE under dilute CMP concentration, denatured type I collagen was resolved by SDS-PAGE and the gel was immersed in a solution of $CF(GPO)_9$ (SEQ ID NO: 10) (6 μM) that had been pre-heated to 85° C. which is above the peptide's melting temperature. After 3 hours of incubation at room temperature followed by washing with deionized water, the gel was photographed using a fluorescent imaging system. The image of the gels showed distinct fluorescent emission from the bands of type I collagen chains (FIG. 28A): not only the α1 and α2 chains were visible but also higher molecular weight bands corresponding to the naturally crosslinked collagen chains were prominently visualized with high fluorescence intensity. Under dilute conditions, the thermally melted CMPs remain mostly in single strands immediately after the cooling due to their slow triple helix folding rate as described above. These monomeric CMPs are able to hybridize with the unfolded collagen chains in the SDS-PAGE which are denatured and densely aggregated in the bands. To estimate the sensitivity of the CMP probe, a dilution series of type I collagen was run. The most dilute band that could be visualized by the $CF(GPO)_9$ (SEQ ID NO: 10) probe contained as little as 5 ng of collagen chains (FIG. 28A, arrow), which is similar to the sensitivity level of the conventional coomassie brilliant blue (CB) staining (FIG. 28A bottom panel). We also found out that enzymatically digested collagen fragments can be readily visualized on SDS-PAGE by the heat activated $CF(GPO)_9$ (SEQ ID NO: 10) just as well as the UV activated caged peptide previously reported from our group (FIG. 25B).

Example 7

Figure 29:
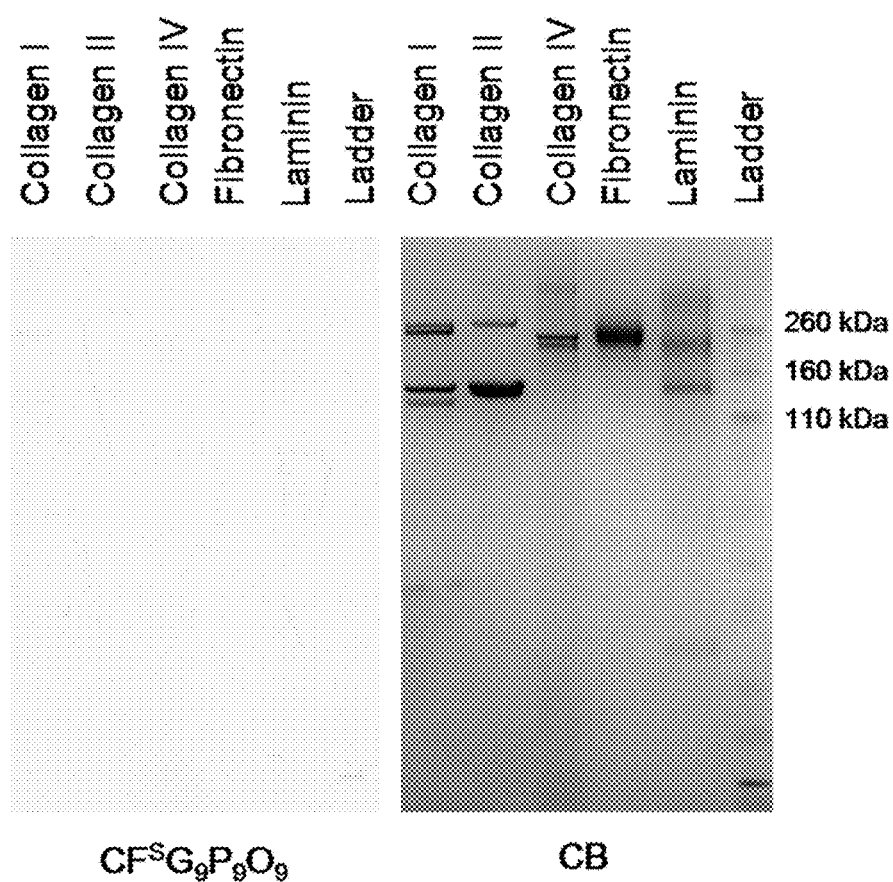
FIG. 29 is an SDS-PAGE of various types of collagens and ECM proteins (each lane is loaded with 2 μg of protein) stained by CF$^S$G$_9$P$_9$O$_9$ (SEQ ID NO: 5) (left) and subsequently by commassie blue (right). The sequence-scrambled CF$^S$G$_9$P$_9$O$_9$ (SEQ ID NO: 5) which lacks triple helical folding capacity showed virtually no binding affinity to the collagen bands.

The binding specificity of $CF(GPO)_9$ (SEQ ID NO: 10) was further determined for different collagen types and other major ECM proteins. Fluorescent images of the gel after SDS-PAGE showed that $CF(GPO)_9$ (SEQ ID NO: 10) binds to collagen types I, II and IV but has no affinity to fibronectin and laminin (FIG. 25C). Same gel stained with the sequence-scrambled peptide CFSG9P9O9 (SEQ ID NO: 5) revealed no collagen bands (FIG. 29). These results clearly show that the CMPs bind by triple helical hybridization and only to proteins with triple helical domains. Intensity of the fluorescence emission in each collagen lane (FIG. 25D) indicated that type IV collagen was stained to a lesser degree than the type I and II collagens. This is most likely because the type IV collagen has lower triple-helical content due to the presence of large globular non-collagenous domains as well as over 20 interruptions in the collagenous domain that break up the triple helix. Finally, when CF(GPO)$_9$ (SEQ ID NO: 10) was used to stain the SDS-PAGE of whole cell lysate of human umbilical vein endothelial cells (HUVEC), no protein band was visualized (FIG. 25E). This result demonstrates the remarkable specificity of the CMP probe for detecting collagen strands.

Example 8

Although the Gly-X-Y triplet repeat is the signature protein sequence of collagen family, similar sequence is also found in several non-collagenous proteins, typically as an oligomerization domain of a larger protein (e.g. mannose binding protein and complement factor C1q). The Gly-X-Y repeats capable of forming triple helical structure are also found on the surface of bacteria and viruses. It was then determined to see if these collagen-like domains can also be detected in SDS-PAGE by CMP binding of the present invention. We tested two proteins: the complement protein C1q, which is constructed of eighteen globular heads connected to six collagen-like triple helical assemblies, and a recombinant protein, Scl2.28CL, derived from the cell-surface protein (Scl2) of Streptococcus pyogenes previously reported to form collagen-like triple helices. The Scl2 assembles into lollipop-like structures similar to C1q and is speculated to interact with mammalian collagens and proteins with collagenous domains (e.g. macrophage scavenger receptor 38), facilitating their adhesion to host cells and tissues. The collagen-like domain of complement factor C1q is rich in Hyp and Pro, which are strong triple helix stabilizers, respectively in the positions X and Y of the Gly-X-Y repeats; however in the Scl2 protein, these positions are populated by charged amino acids which are believed to stabilize collagen triple helix by electrostatic interactions.

Figure 26:
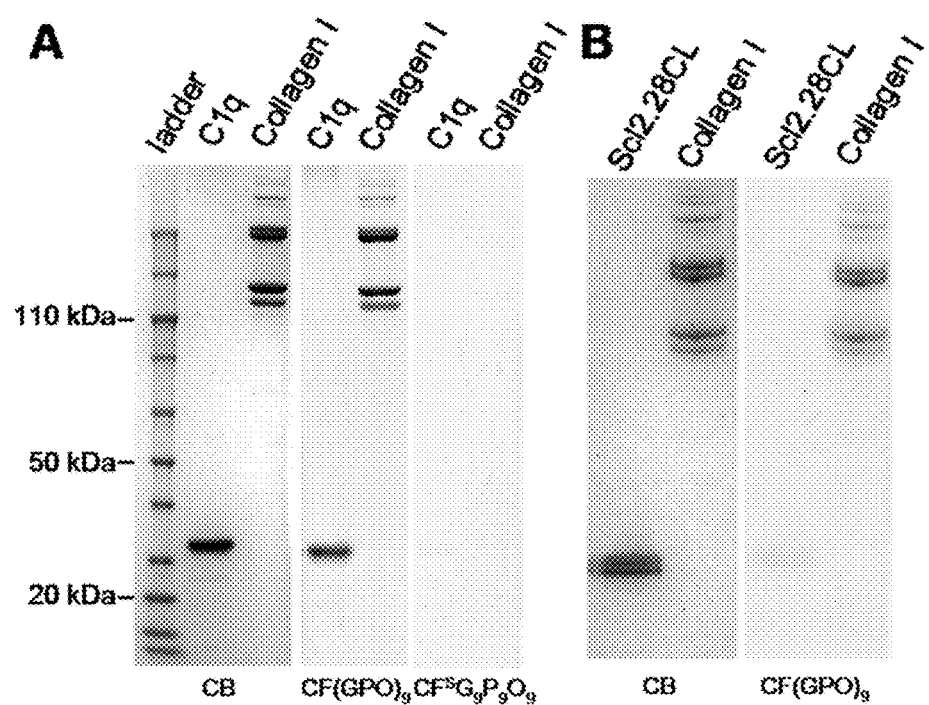
FIG. 26 shows SDS-PAGE of collagen-like proteins stained with CMP. (A) SDS-PAGE loaded with 2 μg of complement factor C1q and type I collagen, stained by CB, CF(GPO)$_9$ (SEQ ID NO: 10), or $^S$G$_9$P$_9$O$_9$ (SEQ ID NO: 5), showing specific visualization of the C1q chains by CF(GPO)$_9$ (SEQ ID NO: 10) hybridization. (B) SDS-PAGE loaded with 2.5 μg of type I collagen and streptococcal collagen-like protein Scl2.28CL stained by CF(GPO)$_9$ (SEQ ID NO: 10), showing almost no staining of the Scl2.28CL band.

It was found that CF(GPO)$_9$ (SEQ ID NO: 10) can stain the SDS-PAGE bands of C1q chains almost as effectively as collagens (FIG. 26A). This indicates that the CMPs are capable of hybridizing with the collagen-like domain of the C1q chains. In drastic contrast, CF(GPO)$_9$ (SEQ ID NO: 10) failed to stain the Scl2.28CL bands (FIG. 26B). In mammalian collagens, hydroxyprolines play a critical role in folding and stabilization of the triple helical structure, while collagen-like domains of bacterial proteins that lack Pro and Hyp rely on charge-charge interactions for making stable triple helix. Heat denatured mammalian collagens partially recover their triple helical structure and turn into gelatin when cooled. The Scl2.28CL chains, however, are unable to refold into triple helix after denaturation. The results indicate that CMP can hybridize with the denatured strands of the Hyp rich collagen and C1q, but it does not make stable heterotrimeric helices with charged collagen-like sequences, most likely because the CMP is a neutral peptide that cannot participate in electrostatic interactions.

Compared to conventional antibody-mediated detection, the CMP probes and methods disclosed herein are more convenient to use. Antibody binding in western blot requires transferring the proteins from PAGE gel onto a polyvinylidene difluoride (PVDF) or nitrocellulose membrane, followed by blocking, and long hours of immunoreactions. In contrast, because of CMP's small size and high affinity, detection of collagen by the CMP probes of the present invention can be performed directly in gels, without transferring and blocking, and in relatively short period of time. In addition, the CMP hybridization relies on protein's overall secondary structure instead of a few well-defined epitopes. Therefore, even fragments of collagen chains can be recognized, a feature useful for studying collagen degradation which is common to many degenerative diseases (e.g. arthritis)

Example 9

Use of caged CMP for immunohistochemistry. Caged CMP, CF$^{NB}$(GPO)$_9$ (SEQ ID NO: 4) was applied to tissue sections (fixed tissue sections from mouse skin, cornea, and bone), followed by exposure to UV light to activate collagen binding. Anti-collagen I antibody (2nd antibody: anti-rabbit-AlexaFluor594) was also applied to the tissue samples for comparison (see Supporting Information Materials and Methods). The decaged CF(GPO)$_9$ (SEQ ID NO: 10) effectively stained the collagen-rich dermis layer of the fixed mouse skin and the stroma of the cornea sections. The control groups stained by scrambled peptide $^S$G$_9$P$_9$O$_9$ (SEQ ID NO: 10) showed no discernible binding under identical experimental conditions (data not shown). The fluorescent signals from the CF(GPO)9 overlapped largely with those from the antibody, which confirmed the specificity of the probes for the collagen fibrils. Compared to the anti-collagen antibody, the CF(GPO)$_9$ (SEQ ID NO: 10) showed more intense signals which also revealed finer details of the collagen fibril organization in the dermis and the corneal stroma. In addition, a bright green line corresponding to the Descemet's membrane of cornea which contains type VIII collagen was clearly visualized by the CMP probe (data not shown). We also noticed that the processing of the tissue seems to enhance the CMP binding. Paraformaldehyde fixed cornea samples were significantly brighter than the fresh unfixed samples when identical CMP staining and imaging protocols were employed. In particular, the mouse tibia bone sections that have undergone acidic demineralization process as well as fixation and paraffin embedding, exhibited strong CF(GPO)$_9$ (SEQ ID NO: 10) signals but almost no collagen antibody signal was detected (data not shown). It is very likely that the tertiary protein structure of the epitopes targeted by the collagen antibody had been compromised by the heat during the paraffin-embedding, and the highly acidic demineralization process; yet the CMP probe can still target such collagens because it recognizes the unfolded secondary protein structure that is prevalent in collagens.

The CMP probe's remarkable ability to target collagens in bones even after acidic demineralization and extensive preservation process demonstrates the robustness and versatility of the CMP mediated collagen staining. Histological preservation and processing often cause alteration or masking of epitopes targeted by immunohistochemical agents. Even for a same target biomolecule, different histological processing (e.g. frozen vs. paraffin-embedded) may require different types of primary antibody. Sometimes, heat- or enzyme-induced antigen retrieval step is necessary to improve the antibody binding. In contrast, CMP probes recognize the secondary protein structure, the metastable polyproline-II-like helix that is waiting for triple helix hybridization partners. For this reason, perturbation of collagen's tertiary and quaternary protein structures seem to have little effect on the CMP's binding affinity to collagen strands.

Example 10

To showcase the CMPs of the present invention ability to identify pathological conditions, a set of healthy and fibrotic rat liver sections were stained utilizing a photo-triggered CMP probe. Two common fibrosis models were tested: a fibrosis induced by repetition of a toxic insult, thioacetamide (TAA), to the liver, and the secondary biliary fibrosis model induced by bile duct ligation (BDL). Because the liver tissues emit strong autofluorescence whose spectrum overlaps with the emission spectrum of CF, TAMRA-NB(GPO)$_9$ (SEQ ID NO: 12) was used for the liver fibrosis staining. In addition, CuSO4 solution was applied to the tissue sections during optical imaging to selectively reduce the lipofuscin-like background autofluorescence. TAMRA-(GPO)$_9$ (SEQ ID NO: 15) staining revealed minimal collagen staining in healthy liver: collagens can only be found surrounding the major vessels in the portal area. In the tissue sections of TAA and BDL fibrotic models, the CMP successfully exposed the abnormal presence of collagens. In the TAA sample, long and thin bridged septa of aggregated collagens were readily seen, and in the BDL model, excess fibrotic collagens were detected around the circular proliferating bile ducts (data not shown). These results are consistent with the hepatic fibrosis patterns for those classical fibrosis models. Compared to Masson Trichrome staining, a common non-immunochemical staining procedure that chemically stains collagen fibers in blue on top of pink colored cellular background, the fluorescent CMP probe offers more clear and collagen specific imaging as well as simultaneous co-staining with other biomarkers that can be easily distinguished by the multi-color channels of fluorescence microscopes (data not shown). The results demonstrate the potential application of CMP probes not only for histology of clinical biopsies, but also for live imaging and targeting of fibrotic tissues.

In summary, the compositions and methods of the present invention has validated the use of fluorescently labeled collagen mimetic peptides for direct and efficient detection of Hyp rich collagenous proteins in SDS-PAGE and immunohistostaining. The results indicate that CMPs are highly effective at staining collagens in extensively processed tissue sections which are not easily probed by conventional antibodies. It is thought that the fluorescent CMPs of the present invention is an excellent alternative to collagen antibodies for detecting fibrous collagens in various assays and tissue imaging. As a potent collagen targeting molecule, CMP is a structurally simple peptide that is easy to prepare and conjugate to other bioactive moieties. The two orthogonal activation mechanisms (heat activation of CMP and light activation of caged CMP) provide great flexibility for the incorporation of additional functionalities to this peptide: the heat activation system is suitable for conjugation of chemically reactive compounds that may be sensitive to UV light or photo-cleaved by-products, while the light activation system is suitable for conjugation of delicate biomolecules (e.g. proteins) that might be incompatible with heat. The ability to synthesize more complex CMP derivatives that can target collagen strands may lead to new applications in tissue scaffold engineering, collagen-targeted drug delivery and in vivo collagen imaging.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A collagen mimetic peptide (CMP) having the formula:

$$L\text{-}S\text{-}[Gly\text{-}X\text{-}Y]_n\text{-}Gly\text{-}X\text{-}Y\text{-}[Gly\text{-}X\text{-}Y]_n; \text{ wherein}$$

L is IRDye-800CW or IRDye 680RD;
S is aminohexanoic acid;
X is proline;
Y is hydroxyproline;
Gly is glycine; and
n is 4.

2. A method for detection of collagen in a subject comprising:
 a) administering to the subject an effective amount of the collagen mimetic peptide of claim 1;
 b) allowing the collagen mimetic peptide, or conjugate or nanoparticle sufficient time to bind collagen and/or gelatin in the subject; and
 c) detecting the collagen mimetic peptide, or conjugate or nanoparticle in the subject.

3. The method of detection of claim 2, wherein the collagen bound in b) is type I collagen.

4. The method of detection of claim 2, wherein the collagen bound in b) is denatured.

5. The method of detection of claim 2, wherein the collagen bound in b) is gelatin.

6. The method of detection of claim 2, wherein the collagen bound in b) is digested by matrix metalloproteases.

7. The method of detection of claim 2, wherein the detection is by the use of fluorescence or near infra-red imaging.

8. A method for detection of collagen remodeling by proteinases in a subject comprising:
 a) administering to the subject an effective amount of the collagen mimetic peptide of claim 1;
 b) allowing the collagen mimetic peptide, or conjugate or nanoparticle sufficient time to bind collagen and/or gelatin in the subject; and
 c) detecting the collagen mimetic peptide, or conjugate or nanoparticle in the subject.

9. A method for detection of pathologic tissues having high proteinase activity in a subject comprising:
   a) administering to the subject an effective amount of the collagen mimetic peptide of claim 1;
   b) allowing the collagen mimetic peptide, or conjugate or nanoparticle sufficient time to bind collagen and/or gelatin in the subject; and
   c) detecting the collagen mimetic peptide, or conjugate or nanoparticle in the subject.

10. A method for detection of collagen remodeling in bones and cartilage in a subject comprising:
   a) administering to the subject an effective amount of the collagen mimetic peptide of claim 1;
   b) allowing the collagen mimetic peptide, or conjugate or nanoparticle sufficient time to bind collagen and/or gelatin in the subject; and
   c) detecting the collagen mimetic peptide, or conjugate or nanoparticle in the subject.

11. A method for detection of musculoskeletal disease in a subject comprising:
   a) administering to the subject an effective amount of the collagen mimetic peptide of claim 1;
   b) allowing the collagen mimetic peptide, or conjugate or nanoparticle sufficient time to bind collagen and/or gelatin in the subject; and
   c) detecting the collagen mimetic peptide, or conjugate or nanoparticle in the subject.

12. The method of claim 11, wherein the musculoskeletal disease is Marfan's Syndrome.

13. A method for treatment of a disease associated with collagen denaturation or remodeling in a subject comprising administering to the subject an effective amount of a collagen mimetic peptide conjugate, or a nanoparticle to treat the disease in the subject.

\* \* \* \* \*